(12) United States Patent
Wakao et al.

(10) Patent No.: US 11,242,541 B2
(45) Date of Patent: Feb. 8, 2022

(54) SKELETAL MUSCLE CELLS AND METHOD FOR INDUCING SAME

(71) Applicant: KYOTO PREFECTURAL PUBLIC UNIVERSITY CORPORATION, Kyoto (JP)

(72) Inventors: Junko Wakao, Kyoto (JP); Tsunao Kishida, Kyoto (JP); Tatsuro Tajiri, Kyoto (JP); Osam Mazda, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 0 days.

(21) Appl. No.: 16/474,416

(22) PCT Filed: Dec. 28, 2017

(86) PCT No.: PCT/JP2017/047305
§ 371 (c)(1),
(2) Date: Jun. 27, 2019

(87) PCT Pub. No.: WO2018/124292
PCT Pub. Date: Jul. 5, 2018

(65) Prior Publication Data
US 2019/0338306 A1 Nov. 7, 2019

(30) Foreign Application Priority Data
Dec. 28, 2016 (JP) .............................. JP2016-255208

(51) Int. Cl.
*C12N 15/85* (2006.01)
*A61K 35/34* (2015.01)
*C07K 14/47* (2006.01)
*C12N 5/077* (2010.01)

(52) U.S. Cl.
CPC .............. *C12N 15/85* (2013.01); *A61K 35/34* (2013.01); *C07K 14/4705* (2013.01); *C12N 5/0656* (2013.01); *C12N 2506/1307* (2013.01)

(58) Field of Classification Search
CPC ............... C12N 15/85; C12N 5/0656; C12N 2506/1307; C12N 15/09; C12N 5/10; A61K 35/34; C07K 14/4705; A61P 21/00
USPC ...................................................... 435/455
See application file for complete search history.

(56) References Cited

U.S. PATENT DOCUMENTS

2013/0040387 A1  2/2013  Heike et al.

FOREIGN PATENT DOCUMENTS

| EP | 0783568 A1 | 7/1997 |
|----|------------|--------|
| JP | 10-505756 A | 6/1998 |
| JP | 2013-527746 A | 7/2013 |
| WO | 96/09373 A1 | 3/1996 |
| WO | 2011/132799 A1 | 10/2011 |

OTHER PUBLICATIONS

Miner et al., Molecular and Cellular Biology, "c-myc Inhibition of MyoD and Myogenin-Initiated Myogenic Differentiation", May 1991; vol. 11, p. 2842-2851. (Year: 1991).*
Lattanzi et al., Journal of Clinical Invest., "High Efficiency Myogenic Conversion of Human Fibroblasts by Adenoviral Vector-mediated MyoD Gene Transfer", May 1998; vol. 101:10, p. 2119-2128. (Year: 1998).*
Tapscott et al., Science, "MyoD1: A Nuclear Phosphoprotein Requiring a Myc Homology Region to Convert Fibroblasts to Myoblasts", Oct. 21, 1988; vol. 242, pp. 405-411. (Year: 1988).*
Conacci-Sorrell et al., Myc-Nick: A cytoplasmic cleavage product of Myc that promotes [alpha]-tubulin acetylation and cell differentiation, Cell., 142(3):480-493 (2010).
Davis et al., Expression of a single transfected cDNA converts Fibroblasts to Myoblasts, Cell, 51:987-1000 (1987).
European Application No. 17888624.8, European Search Report and Opinion, dated Jun. 9, 2020.
International Application No. PCT/JP2017/047305, International Preliminary Report on Patentability, dated Jul. 11, 2019.
International Application No. PCT/JP2017/047305, International Search Report and Written Opinion, dated Mar. 27, 2018.
Ishibashi et al., MyoD induces myogenic differentiation through cooperation of its NH2- and COOH-terminal regions, J. Cell Biol., 171(3):471-482 (2005).
Lattanzi et al., High efficiency myogenic conversion of human fibroblasts by adenoviral vector-mediated MyoD gene transfer, J. Clin. Invest., 101(10):2119-2128 (1998).
Margariti et al., Direct reprogramming of adult cells: avoiding the pluripotent state, Stem Cells Cloning: Advances and Applications, 7:19-29 (2014).
Miner et al., c-myc inhibition of MyoD and myogenin-initiated myogenic differentiation, Mol. and Cell. Biol., 11(5):2842-2851 (1991).
Shoji et al., Early pathogenesis of Duchenne muscular dystrophy modelled in patient-derived human induced pluripotent stem cells, Sci. Rep., 5(12831): 1-5 (2015).
Song et al., Setdb1 Is Required for Myogenic Differentiation of C2C12 Myoblast Cells via Maintenance of MyoD Expression, Mol Cells, 38(4):362-372 (2015).
Takahashi et al., Induction of pluripotent stem cells from adult human fibroblasts by defined factors, Cell, 131(5):861-872 (2007).
Tanaka et al., Efficient and Reproducible Myogenic Differentiation from Human iPS Cells:Prospects for Modeling Miyoshi Myopathy In Vitro, Pios One, 8(4):e61540 (2013).
Wakao et al., Efficient direct conversion of humn fibroblasts into myogenic lineage induced by co-transduction with MYCL and MYODI, Biochem. Biophy. Res. Comm., 488(2):368-373 (2017).
Xiao et al., Regulation of alpha7 integrin expression during muscle differentiation, J. Biol. Chem., 278(50):49780-49788 (2003).

* cited by examiner

*Primary Examiner* — Christopher M Babic
*Assistant Examiner* — Alexander W Nicol
(74) *Attorney, Agent, or Firm* — Marshall, Gerstein & Borun LLP

(57) ABSTRACT

Provided is a method for inducing a skeletal muscle cell including a step of introducing MyoD family gene or an expression product thereof and Myc family gene or an expression product thereof into a somatic cell of a mammal.

11 Claims, 25 Drawing Sheets

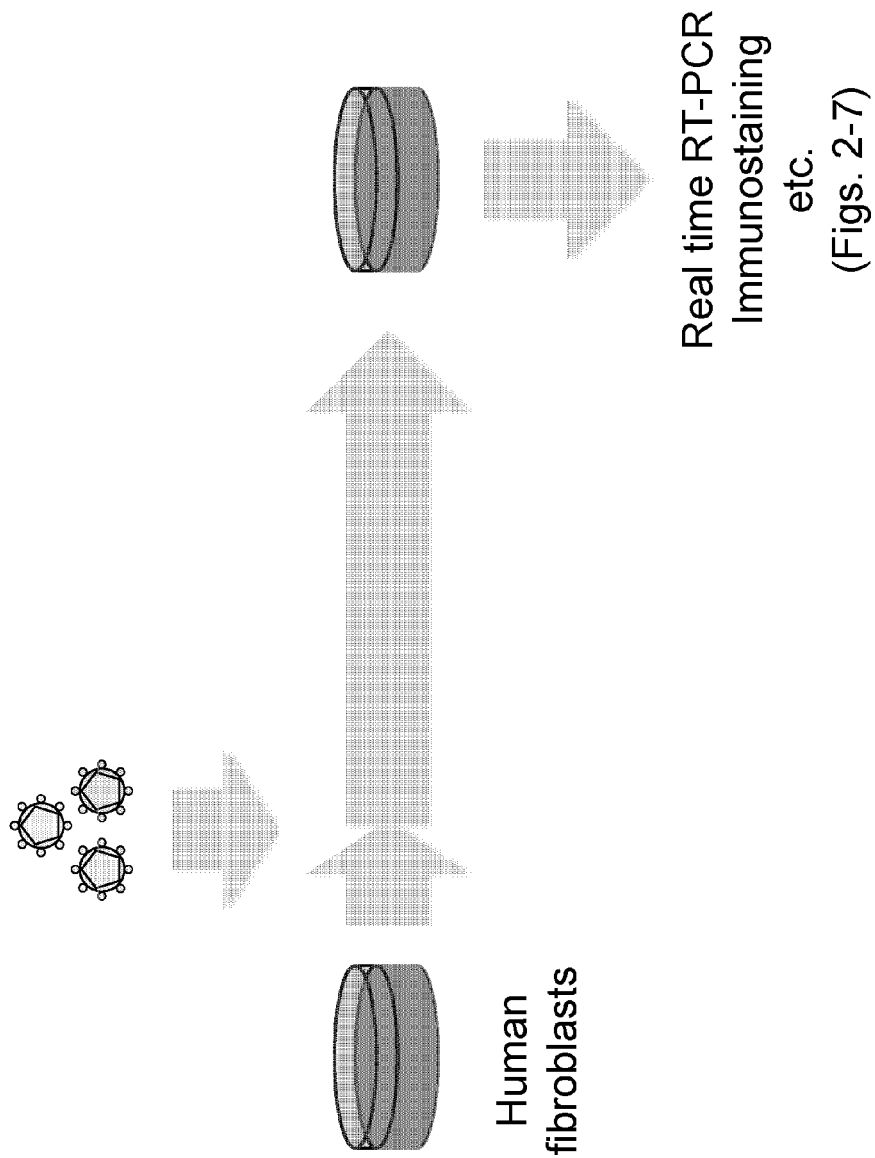

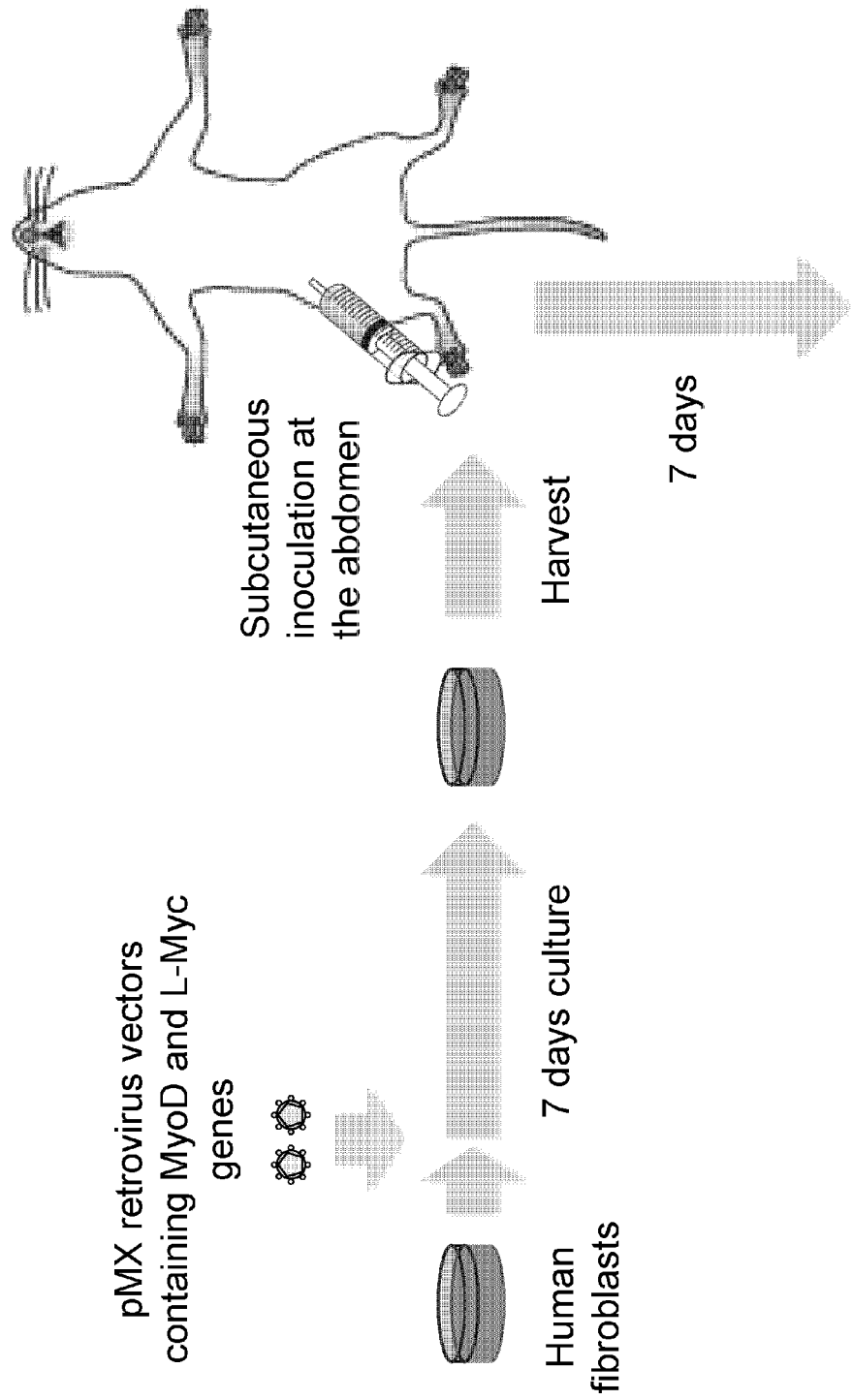

Graft: HDFs
Paraffin section

Anti-Desmin

× 200

HE staining

Graft: MyoD + L-Myc transduced cells
Paraffin section

Fig. 12
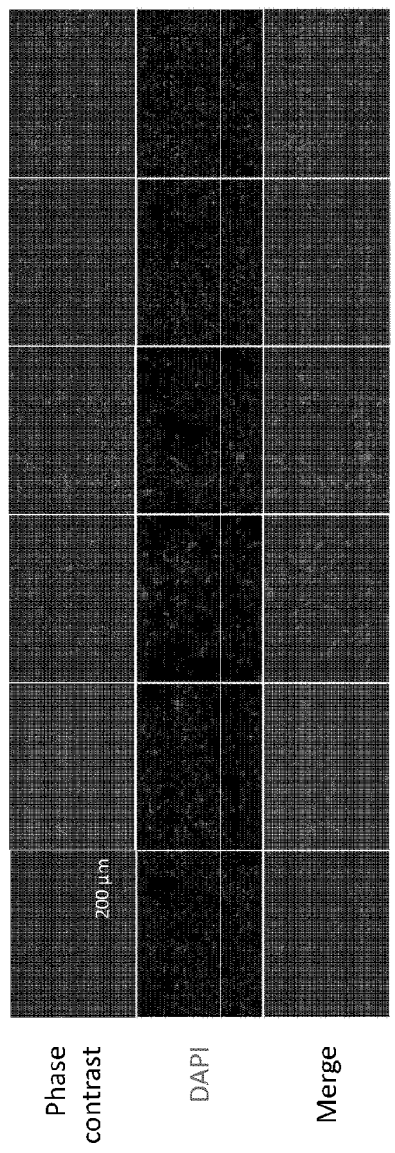
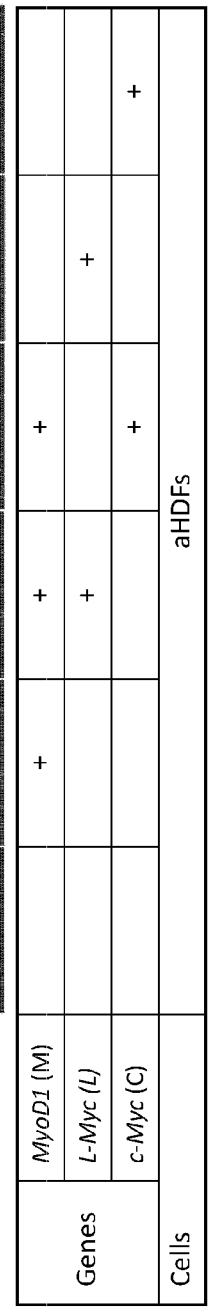
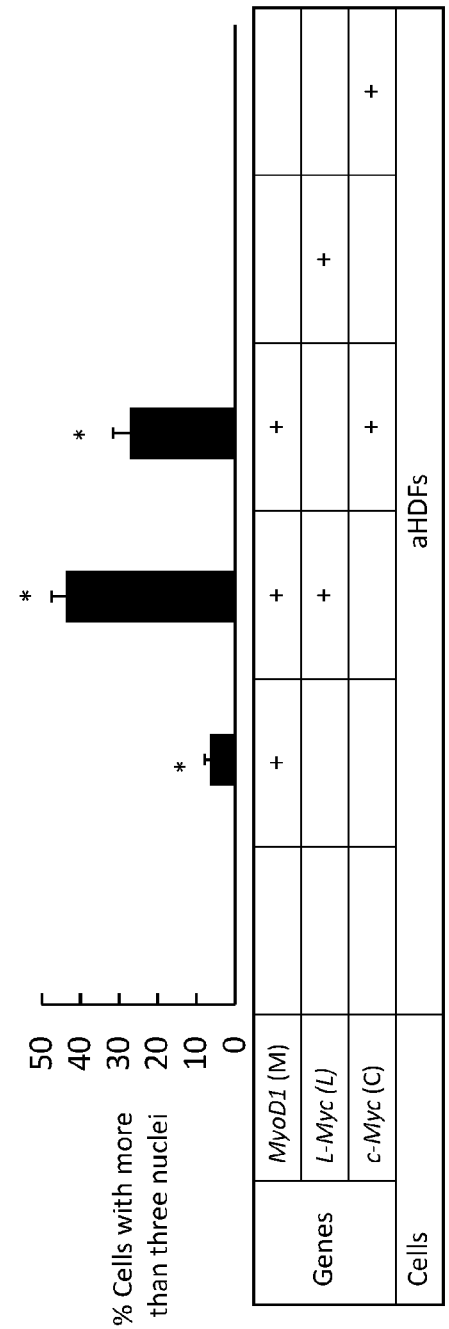

Fig. 17
Desmin
+ DAPI
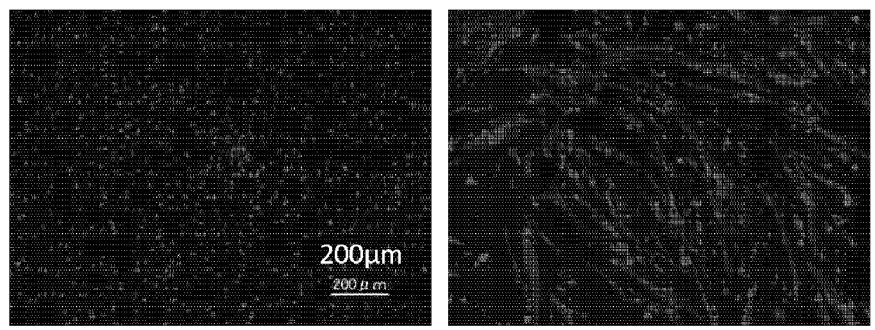
CKM
+ DAPI
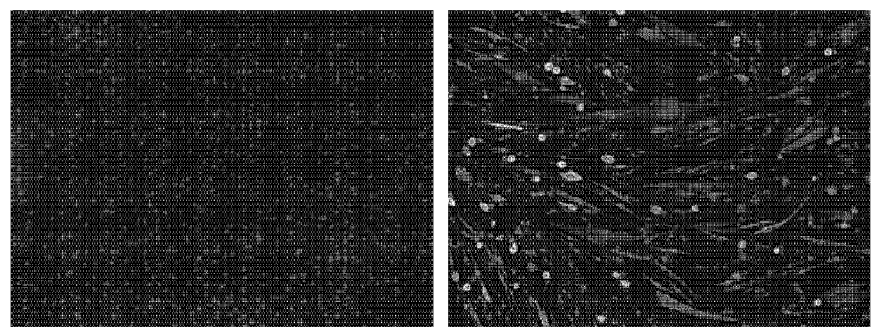
| Genes | - | ML |
|---|---|---|
| Cells | aHDFs ||

# SKELETAL MUSCLE CELLS AND METHOD FOR INDUCING SAME

TECHNICAL FIELD

The present invention mainly relates to a skeletal muscle cell and an induction method thereof. More particularly, it relates to a method for inducing a skeletal muscle cell by direct reprogramming.

BACKGROUND ART

Muscle is an essential tissue for animal exercise and is composed of filamentous multinucleated cells having contractile activity. In induction of differentiation of skeletal muscle, mononuclear myoblasts are differentiated and fused to form multinucleated muscle cells. It is known that differentiation induction of skeletal muscle is controlled by transcription factors such as MyoD family and MEF2 family.

If muscles can be regenerated and transplanted in diseases such as congenital abnormalities of muscles such as diaphragmatic agenesis and the like, hereditary diseases of muscles such as muscular dystrophy and the like, muscle defects caused by severe trauma or surgical treatment, and the like, it may become an effective new regenerative medicine.

It has long been known that myoblast-like cells can be induced by introducing a skeletal muscle-specific transcription factor, a gene of the MyoD family, into mouse fibroblasts. However, in human fibroblasts, there is a problem that even if a gene of MyoD family is introduced, myoblasts cannot be induced to the same extent as mouse.

DOCUMENT LIST

Non-Patent Document non-patent document 1: Davis R L, Weintraub H, Lassar A B. Expression of a single transfected cDNA converts fibroblasts to myoblasts. Cell. 1987 Dec. 24; 51(6):987-1000.

SUMMARY OF THE INVENTION

Problems to be Solved by the Invention

The present invention aims to provide a method for inducing skeletal muscle cells that can be applied to a treatment of a disease accompanying muscle defect and the like.

Means of Solving the Problems

The present inventors have found that skeletal muscle cells can be obtained directly by introducing MyoD gene and L-myc gene in combination into somatic cells of a mammal (direct reprogramming) without conversion into pluripotent stem cells, such as ES cells and iPS cells. The present invention has been completed by performing further studies based on such findings.

The present invention encompasses the following invention.

Item 1

A method for inducing (generating) a skeletal muscle cell, comprising a step of introducing MyoD family gene or an expression product thereof and Myc family gene or an expression product thereof into a somatic cell of a mammal.

Item 2

The method of item 1, wherein the aforementioned somatic cell is a fibroblast.

Item 3

The method of item 1, wherein the aforementioned somatic cell is a somatic cell of human.

Item 4

The method of item 1 or 2, wherein the MyoD family gene is MyoD1 gene and the Myc family gene is L-myc gene.

Item 5

A skeletal muscle cell derived from a somatic cell of a mammal and having exogenous MyoD family gene or an expression product thereof and Myc family gene or an expression product thereof.

Item 6

The skeletal muscle cell of claim 5, which is obtained by the method of any one of items 1 to 4.

Item 7

A transplantation material comprising a cell obtained by the method of any one of items 1 to 4 or the skeletal muscle cell of item 4 for the treatment of a disease based on defect, deficiency or loss of function of skeletal muscle.

Item 8

A composition for inducing (generating) a skeletal muscle cell, comprising MyoD family gene or an expression product thereof and Myc family gene or an expression product thereof.

Effect of the Invention

According to the present invention, skeletal muscle cells can be prepared from somatic cells by direct reprogramming in a short period of time. The skeletal muscle cells can be induced easily from somatic cells of a person who undergoes transplantation. Accordingly, when skeletal muscle cells are transplanted, problems, such as an immunological rejection response, do not occur. In addition, skeletal muscle cells can be induced directly from somatic cells without conversion into iPS cells or ES cells, and hence problems due to pluripotent stem cells, such as carcinogenesis, can be avoided.

BRIEF DESCRIPTION OF THE DRAWINGS

FIG. 3-1 shows the results of immunofluorescence staining (CKM).
FIG. 3-2 shows the results of immunofluorescence staining (Dystrophin).
FIG. 3-3 shows the results of immunofluorescence staining (Myogenin).
FIG. 8A shows the outline of the method of Example 8.

FIG. 9-1 shows the results of immunohistochemical staining of tissue transplanted with fibroblasts. Paraffin section, ×200 magnification.

FIG. 9-2 shows the results of immunohistochemical staining of tissue transplanted with MyoD1 and L-Myc. Paraffin section, ×200 magnification.

FIG. 12 (A) shows the results of nuclear staining. (B) shows the measurement results of percentage of the number of cells with more than 3 nuclei to the total number of cells.

FIG. 17 shows the results of immunofluorescence staining of Desmin and CKM.

DESCRIPTION OF EMBODIMENTS

Figure 2:
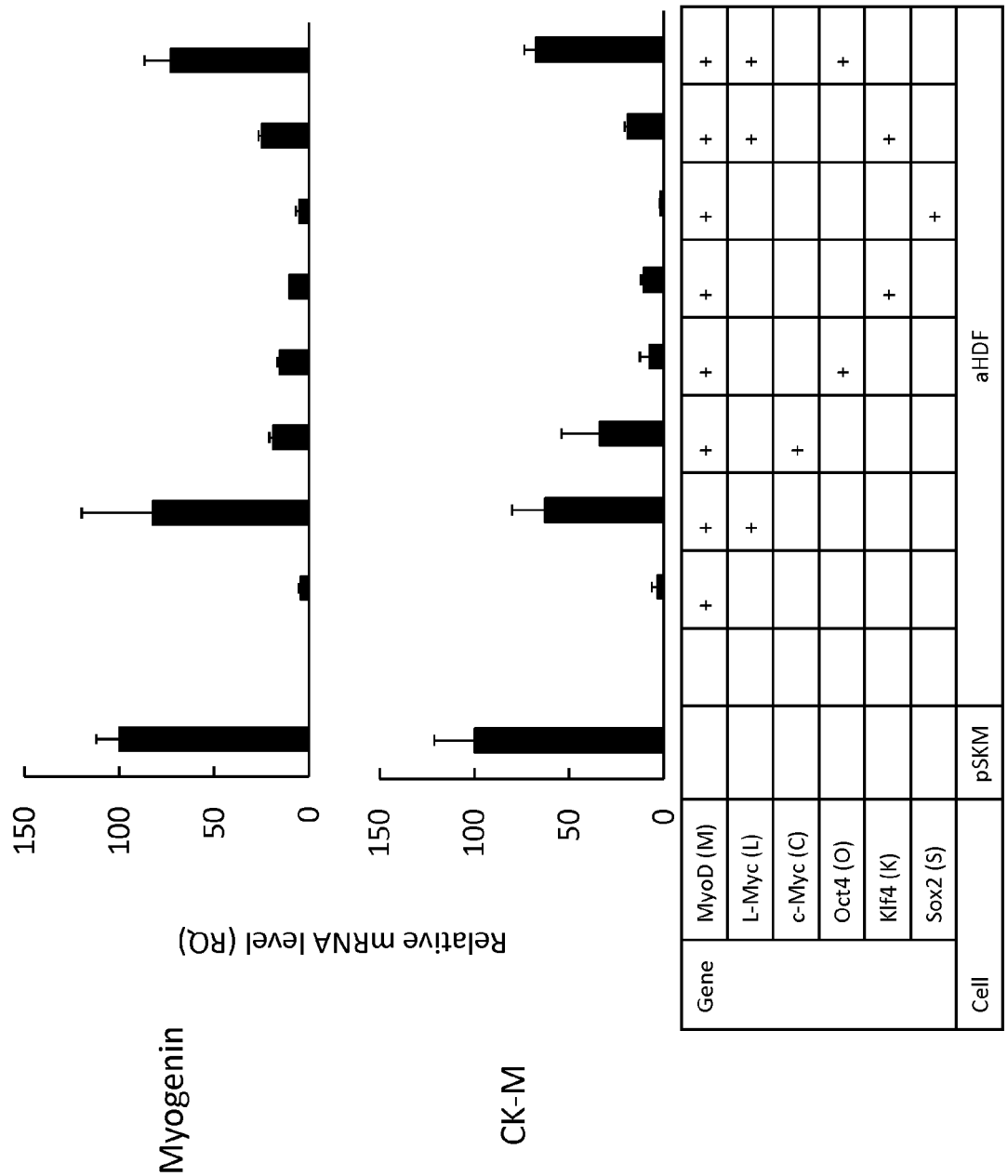
FIG. 2 shows mRNA expression measurement results of Myogenin gene and CKM gene.

The present invention relates to a method for inducing a skeletal muscle cell by converting a mammalian differentiated somatic cell into a skeletal muscle cell. The term "convert" herein means changing a somatic cell into a target skeletal muscle cell. One preferred embodiment of the method of the present invention provides a method of converting a somatic cell into a skeletal muscle cell without reprogramming of cells, such as production of iPS cells, which is also called "direct reprogramming" or "direct conversion."

Induction into a skeletal muscle cell can be performed either in vitro or in vivo.

During the normal process of development of skeletal muscle, myoblasts fuse into multinucleated myotube cells and mature into myofibers. Normal skeletal muscle tissue contains muscle satellite cells capable of functioning as stem cells. In the present specification, myoblast, muscle satellite cell, myotube cell, myotube, myofiber, mature myofiber and the like are collectively referred to as skeletal muscle cell or muscle cell.

Skeletal muscle refers to muscles other than cardiac muscle and smooth muscle among animal muscles. Of the striated muscle and smooth muscle, skeletal muscle belongs to the striated muscle. Skeletal muscle cells are multinucleated cells, and muscle fiber is produced from many myoblasts.

Skeletal muscle cell is derived from mesenchymal stem cell. In differentiation in vivo, mesenchymal stem cell is differentiated into myoblast and many myoblasts are fused to form myotube cell.

Obtainment of skeletal muscle cell can be evaluated based on gene expression and protein expression of skeletal muscle-specific markers such as Myogenin, creatine kinase muscle (CKM), Myosin heavy chain 3 (MHC 3) and the like, and morphological features such as formation of multinucleus and muscle fibers, functions such as contractile activity and the like.

Somatic Cell

Any somatic cells derived from mammals can be used. When skeletal muscle cells are transplanted to a living body, somatic cells (autologous cells) derived from a test subject who undergoes transplantation are preferably used to reduce risks of infection, rejection responses, and the like. However, instead of the autologous cells, skeletal muscle cells prepared in advance from somatic cells of other persons or other animals may be used for, for example, transplantation for muscle deficiency or the like. Alternatively, skeletal muscle cells can be prepared from somatic cells of another person or another animal prepared in advance, and used for transplantation. That is, a skeletal muscle cell bank can be prepared in advance, and used for transplantation. In such a case, in order to reduce risks, such as rejection responses, MHC typing can be carried out in advance. Further, cell properties and tumorigenicity of skeletal muscle cells can be confirmed in advance.

In the present specification, examples of mammals include mice, rats, hamsters, humans, dogs, cats, monkeys, rabbits, cows, horses, pigs, and the like, particularly humans.

The somatic cell as the subject of the method of the present invention (direct reprogramming) is not particularly limited.

As the somatic cell, a somatic cell that can be easily collected from a living body can be used. Examples thereof include fibroblasts, keratinocytes, oral mucosal epithelial cells, nasal mucosal epithelial cells, respiratory mucosal epithelial cells, gastric mucosal epithelial cells, intestinal mucosal epithelial cells, vascular endothelial cells, smooth muscle cells, adipocytes, gingival cells (gingival fibroblasts and gingival epithelial cells), dental pulp cells, periodontal ligament cells, bone marrow cells, bone marrow-derived interstitial cells, leukocytes, lymphocytes, conjunctival epithelial cells, and osteoclasts, preferably fibroblasts, keratinocytes, oral mucosal epithelial cells, gingival cells, leukocytes, and lymphocytes. In the present invention, the above-mentioned cell collected from a living body is preferably used.

Gene or Expression Product Thereof

In the method of the present invention, MyoD family gene or an expression product thereof and Myc family gene or an expression product thereof are introduced into somatic cells. As used herein, the "expression product" is, for example, mRNA or protein of MyoD family gene or L-myc gene.

In the method of the present invention, micro RNA, siRNA, shRNA and DNA expressing them can also be used in addition to the MyoD family gene or an expression product thereof and Myc family gene or an expression product thereof. In addition, various proteins can also be used in combination. From the viewpoint of efficiency with which skeletal muscle cells can be obtained and from the viewpoint of convenience, it is preferable to use two genes of MyoD family gene and Myc family gene, for example, two genes alone of MyoD1 gene and L-myc gene.

MyoD family gene is a group of genes encoding bHLH (basic helix loop helix) type transcription factors involved in the control of differentiation of muscle. Examples of the MyoD family gene include MyoD1, Myf5, myogenin and MRF4. In the present invention, the MyoD family gene is preferably MyoD1 gene.

Myc family gene also encodes bHLH (basic helix loop helix) type transcription factors. Examples of the Myc family gene include c-myc, N-myc and L-Myc. In the present invention, the Myc family gene is preferably L-Myc.

All of the above genes are highly conserved in vertebrates. In this specification, they refer to genes including homologues, unless a specific animal name is described. The genes further include genes having functions equivalent to those of wild-type gene products, even when the genes include mutations including polymorphisms.

For example, cDNA base sequences of human (Homo sapiens) MyoD1 gene and L-myc gene, and amino acid sequences of proteins encoded by these sequences, have been registered at GenBank provided by the National Center for Biotechnology Information (NCBI), under the following accession numbers (it should be understood that when multiple revisions have been registered, each number refers to the latest revision):

human MyoD1 gene cDNA sequence: NM_002478 (e.g., NM_002478.4),
human MyoD1 protein amino acid sequence: NP_002469 (e.g., NP_002469.2);
human L-myc gene cDNA sequence: NM_001033081, NM_001033082, NM_005376 (e.g., NM_001033081.2, NM_001033082.2, NM_005376.4),
human L-myc protein amino acid sequence: NP_001028253.1, NP_001028254.2, NP_005367.2 (e.g., NP_001028253, NP_001028254, NP_005367).

Introduction

The method of the present invention can be performed according to a known direct reprogramming method, except that specific genes are selected. For example, the method can be performed according to the method described in any one of the following documents:

1: Direct reprogramming of fibroblasts into functional cardiomyocytes by defined factors. Masaki Ieda, Ji-Dong Fu, Paul Delgado-Olguin, Vasanth Vedantham, Yohei Hayashi, Benoit G. Bruneau, and Deepak Srivastava, Cell, 142: 375-386, 2010.
2: Direct conversion of fibroblasts to functional neurons by defined factors. Thomas Vierbuchen, Austin Ostermeier, Zhiping P. Pang, Yuko Kokubu, Thomas C. Sudhof & Marius Wernig, Nature, 463: 1035-1041, 2010
3: Induction of human neuronal cells by defined transcription factors. Pang Z P, Yang N, Vierbuchen T, Ostermeier A, Fuentes D R, Yang T Q, Citri A, Sebastiano V, Marro S, Sudhof T C, Wernig M, Nature, 476: 220-223, 2011.
4: Generation of hyaline cartilaginous tissue from mouse adult dermal fibroblast culture by defined factors, Kunihiko Hiramatsu, Satoru Sasagawa, Hidetatsu Outani, Kanako Nakagawa, Hideki Yoshikawa, and Noriyuki Tsumaki, Journal of Clinical Investigation, 121: 640-657, 2011.
5: Induction of functional hepatocyte-like cells from mouse fibroblasts by defined factors. Pengyu Huang, Zhiying He, Shuyi Ji, Huawang Sun, Dao Xiang, Changcheng Liu, Yiping Hu, XinWang & Lijian Hui, Nature, 475: 386-389, 2011.
6: Direct conversion of mouse fibroblasts to hepatocyte-like cells by defined factors. Sayaka Sekiya & Atsushi Suzuki, Nature, 475: 390-393, 2011.
7: Direct conversion of human fibroblasts into functional osteoblasts by defined factors. Yamamoto K, Kishida T, Sato Y, Nishioka K, Ejima A, Fujiwara H, Kubo T, Yamamoto T, Kanamura N & Mazda O. Proc Natl Acad Sci USA. 112:6152-6157, 2015.
8: Reprogrammed Functional Brown Adipocytes Ameliorate Insulin Resistance and Dyslipidemia in Diet-Induced Obesity and Type 2 Diabetes. Kishida T, Ejima A, Yamamoto K, Tanaka S, Yamamoto T, Mazda O. Stem Cell Reports. 5: 569-581, 2015.
9: Generation of directly converted human osteoblasts that are free of exogenous gene and xenogenic protein. Yamamoto K., Sato Y., Honjo K., Ichioka H., Oseko F., Sowa Y., Yamamoto T., Kanamura N., Kishida T., Mazda O. J Cell Biochem 117:2538-2545, 2016.
10: WO 2014/010746

The contents of Documents 1 to 10 are incorporated herein by reference.

Specifically, it is preferable to incorporate the object gene into one or plural expression vectors and introduce the expression vector into target somatic cells to express the gene in the cells.

As a method of introducing a gene, there can also be used, for example, a method involving infection with a viral vector, such as a retrovirus vector, an adenovirus vector, a lentivirus vector, an adeno-associated virus vector, a herpesvirus vector, or a Sendai virus vector; and in the case of introduction of a gene and an expression product thereof, a method involving transfection with a plasmid vector, an episomal vector, or a gene expression product (mRNA, protein) by a non-viral vector, such as a cationic liposome, a cationic polymer, or electroporation. Alternatively, mRNA can also be introduced. In this description, all of the means to be used for gene introduction are collectively referred to as "vector".

From the aspects of introduction efficiency and stable maintenance of the introduced gene, a virus vector is preferable, and plasmid is preferable to suppress the risk of canceration.

By introducing a drug selective marker (conferring resistance to puromycin, blasticidin S, neomycin, hygromycin, etc.) with an object gene and then performing drug selection, cells that express the object gene can be selected and then used.

Introduction of gene in the present invention may be performed using a plasmid or a virus vector, for example, retrovirus vector, may also be used. From the aspects of introduction efficiency and stable maintenance of the introduced gene, a virus vector is preferable, and plasmid is preferable to suppress the risk of canceration.

The gene introduced into somatic cells can be transcribed by an LTR promoter, or may be expressed from another promoter in a vector. For example, constitutive expression promoters, such as CMV promoter, EF-1α promoter, and CAG promoter, or desired inductive promoters may be used. Alternatively, a chimeric promoter obtained by replacing a portion of LTR with another promoter may also be used.

When the factor to be introduced is an expression product of a gene (such as a protein), a peptide called "protein transduction domain (PTD)" and the like may be bonded to a protein obtained as an expression product, and added to a medium to introduce the peptide into somatic cells.

Culture

In the method of the present invention, differentiated somatic cells of mammals can be cultured in a medium after gene introduction. For example, it is a preferable embodiment when inducing (generating) skeletal muscle cell in vitro.

The culture can be performed in an appropriate container for containing the cells and medium. A preferred example of the technique of performing the culture is, but is not limited to, a technique of performing the culture at about 37° C. at a carbon dioxide concentration of about 5%. The culture under such conditions can be performed by using, for example, a known $CO_2$ incubator.

The culture period is not particularly limited as long as the effect of the present invention is not impaired. For example, it can be set to about 12 hours to one month, about one day to 3 weeks, about 3 days to 2 weeks. Where necessary, the medium may be exchanged. The culture conditions preferably follow those of a conventional method.

In culture, passage can be performed as necessary. When passage is performed, the cells are collected before or immediately after the cells reach confluence, and the cells are seeded in fresh medium. In the culture of the present invention, the medium can be appropriately replaced.

Medium

The medium used in the method of the present invention is not particularly limited. Usual liquid media such as DMEM (Dulbecco's Modified Eagle's Medium), EMEM (Eagle's Minimal Essential Medium), αMEM (alpha Modified Minimum Essential Medium) and the like can be used. If necessary, serum components (Fetal Bovine Serum (FBS), Human Serum (HS)), antibacterial agents, such as streptomycin and penicillin, non-essential amino acids (NEAA), and like components can be added.

It is also possible to add a growth factor such as IGF-1 or the like.

In view of the high efficiency in the generation of skeletal muscle cells by the method of the present invention, the use of a differentiation-inducing medium for differentiation of skeletal muscle cells as a medium is preferable. The "differentiation-inducing medium for inducing skeletal muscle cells" refers to a medium containing components that allow pluripotent stem cells (such as ES cells or iPS cells) to differentiate into skeletal muscle cells.

The differentiation-inducing medium for differentiation of skeletal muscle cells is not particularly limited. Examples thereof include, but are not limited to, a medium for myoblast differentiation (αMEM medium added with 1% Non-Essential Amino Acids (NEAA) and 5% Horse Serum and supplemented with IGF-1 10 ng/ml, 100 U/mL Penicillin and 100 µg/ml Streptomycin).

Induction (Generation)

Thus, a skeletal muscle cell is induced from a somatic cell.

In one embodiment, the induced skeletal muscle cell contains exogenous MyoD family gene and Myc family gene. The term "exogenous" as used herein means an embodiment of a gene or an expression product thereof that is introduced mainly by the above introduction means and that is different from native embodiment. Examples of the embodiment include genes whose expression is controlled by a promoter other than native promoters, genes present at non-native chromosomal loci, extrachromosomal genes, and the like.

The skeletal muscle cell may be obtained as a mixture with a cell other than skeletal muscle cell (e.g., original somatic cell). In this case, the skeletal muscle cell can be separated from the cell other than skeletal muscle cell as necessary. The means for separation is not particularly limited. For example, they can be separated using a cell sorter or magnetic beads.

The skeletal muscle cell induced by the present invention can be preferably used as, for example, the below-mentioned transplantation material.

The skeletal muscle cell induced by the present invention can also be used for, for example, various studies and development of technologies using skeletal muscle cells. For example, the present invention is useful for basic studies such as analysis of the development of skeletal muscle, differentiation, mechanisms of morphogenesis, mechanical stress against these factors, and influences of nutrients and hormones.

The use of the skeletal muscle cell induced by the present invention allows skeletal muscle cells to be established from humans or animals having various diseases or genetic backgrounds in a simple, rapid, and inexpensive manner. Accordingly, abnormalities in skeletal muscle cells related to the diseases or genetic backgrounds can be analyzed by, for example, a biochemical, molecular biological, or immunological technique. This can contribute to studies on clarification of pathogenic mechanisms of diseases and the like, or development of diagnostic methods. Development of drugs, toxicity tests of drugs, and the like using such skeletal muscle cells can contribute to the development of novel treatment methods for various diseases.

Transplantation Material

The skeletal muscle cell induced by the present invention can be used for treating various diseases. In this case, the skeletal muscle cell may be provided in the form of a transplantation material.

The transplantation material refers to a skeletal muscle-containing material to be introduced into a living body for repair and reconstruction of muscular tissue (particularly, myofiber). The skeletal muscle cells obtained in the present invention can be used for preparation of the transplantation material. The skeletal muscle cells themselves can also be used as the transplantation material. Accordingly, the skeletal muscle cells can be transplanted to a patient as a cell preparation, can be transplanted together with a base (scaffold (e.g., amniotic membrane, biocompatible polymer and the like)) formed of an artificial material, or can be cultured with a scaffold, and then transplanted.

The target diseases of the above-mentioned treatment include diseases based on defects or lack of skeletal muscle cells such as muscle damage due to trauma or injury, sarcopenia, congenital diaphragmatic hernia, omphalocele, gastroschisis, umbilical hernia, abdominal wall scar hernia after abdominal surgery and the like;

diseases based on reduced skeletal muscle function such as prune belly syndrome, Polish syndrome, anorectal malformation (anal atresia), inguinal hernia, disuse syndrome after long-term bed rest and the like;

inflammatory myopathies such as dermatomyositis/polymyositis, sporadic inclusion body myositis, myositis associated with viral infection, myositis associated with mycoplasma infection, and the like;

metabolic myopathies such as glycogenosis type II (Pompe disease), glycogenosis type III, glycogenosis type V (McArdle disease), glycogenosis type VII (Tarui disease) and the like; muscular dystrophy, myopathy, myasthenia gravis, congenital myasthenic syndrome, mitochondrial disease, amyotrophic lateral sclerosis (ALS), other muscle diseases and the like.

In the present specification, unless otherwise specified, the term "treatment" refers to management for a patient suffering from a specific disease or disorder, and means to ameliorate the severity of the disease or disorder, ameliorate one or more symptoms thereof, or delay or reduce the speed of progress of the disease or disorder. In this specification, "treatment" includes "prevention".

The skeletal muscle cell obtained in the present invention may be used not only for treatment of a disease, but also for beauty or functional enhancement. In such a case, for expediency, management for humans is also referred to as treatment in this specification, the term "patient" can be replaced by the term "healthy subject" or "human," and the term "disease" can be replaced by the term "beauty" or "function".

The present invention can also be used not only for treatment for diseases of humans, but also for treatment for diseases of mammals including pets, such as dogs and cats; and livestock, such as cattle, horses, swine, sheep, and chickens. In such a case, the term "patient" is replaced by the term "affected livestock" or "mammal".

Composition

As described above, a skeletal muscle cell can be induced by introducing MyoD family gene or an expression product thereof and Myc family gene or an expression product thereof into a somatic cell. Therefore, the present invention further provides a composition containing MyoD family gene or an expression product thereof and Myc family gene or an expression product thereof for inducing skeletal muscle cells. The composition for inducing a skeletal muscle cell contains factor(s) used for inducing a skeletal muscle cell from a somatic cell, in which MyoD family gene or an expression product thereof and Myc family gene or an expression product thereof are desirably contained in a form permitting introduction into a somatic cell. The above-mentioned form permitting introduction of genes into a somatic cell is specifically, for example, a vector incorporating the above-mentioned genes. As used herein, the above-mentioned genes may be incorporated in different vectors, or two or more kinds of genes may be simultaneously incorporated in a single vector.

The kind and the like of a usable vector are as described above.

The above-mentioned composition can be used, for example, as a medicament (therapeutic drug) in gene therapy.

Direct•Reprogramming In Vivo

By introducing MyoD family gene or an expression product thereof and Myc family gene or an expression product thereof into fibroblasts present at a site lacking skeletal muscle and the like, skeletal muscle cells are induced at the damaged site by direct•reprogramming, which in turn can contribute to the treatment of damaged skeletal muscle and regeneration of skeletal muscle. The above-mentioned composition of the present invention can be preferably used for the introduction of MyoD family gene or an expression product thereof and Myc family gene or an expression product thereof.

The induction method of the present invention is appreciated to include the above-mentioned direct• reprogramming in vivo in addition to direct•reprogramming in vitro. Such direct•reprogramming in vivo makes it possible to perform, for example, gene therapy to treat various diseases. Specific examples of the disease include those described above.

Direct•reprogramming in vivo can be performed according to, in addition to the introduction of MyoD family gene or an expression product thereof and Myc family gene or an expression product thereof into fibroblasts at the site of damaged skeletal muscle, for example, direct• reprogramming in vivo into cardiac muscle cells described in the following documents.

1: Ieda M. Heart regeneration using reprogramming technology. Proc Jpn Acad Ser B Phys Biol Sci. 2013; 89(3):118-28. Review.
2: Ieda M, Fu J D, Delgado-Olguin P, Vedantham V, Hayashi Y, Bruneau B G, Srivastava D. Direct reprogramming of fibroblasts into functional cardiomyocytes by defined factors. Cell. 2010 Aug. 6; 142(3):375-86.
3: Qian L, Huang Y, Spencer C I, Foley A, Vedantham V, Liu L, Conway S J, Fu J D, Srivastava D. In vivo reprogramming of murine cardiac fibroblasts into induced cardiomyocytes. Nature. 2012 May 31; 485(7400):593-8.

The contents of the above-mentioned documents 1 to 3 are incorporated in the present specification by reference.

EXAMPLES

While the Examples are shown below, the present invention is not limited to the Examples alone.

In the Examples, HDF refers to Human Dermal Fibroblast.

Figures 1, 3:
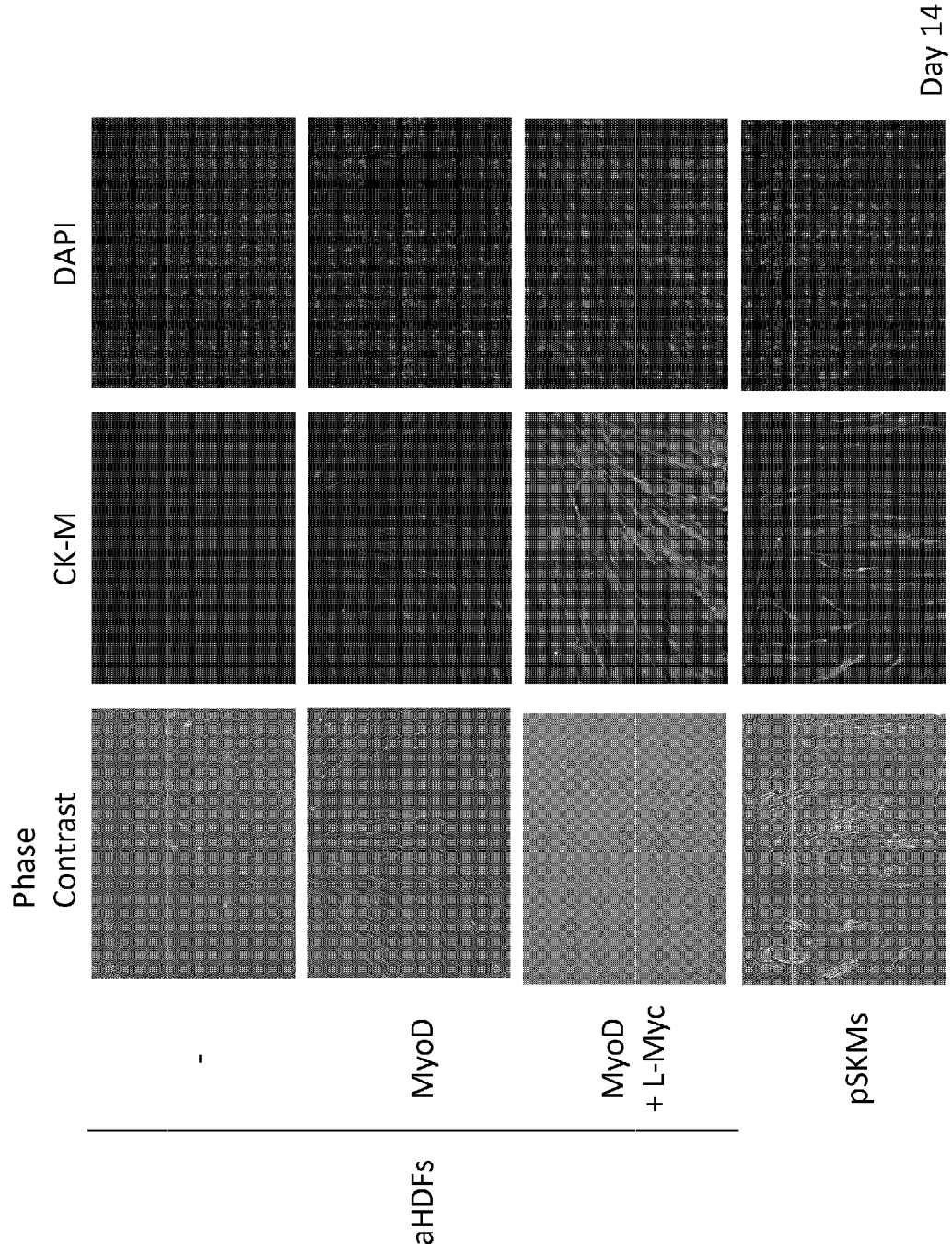
Figures 2, 3:
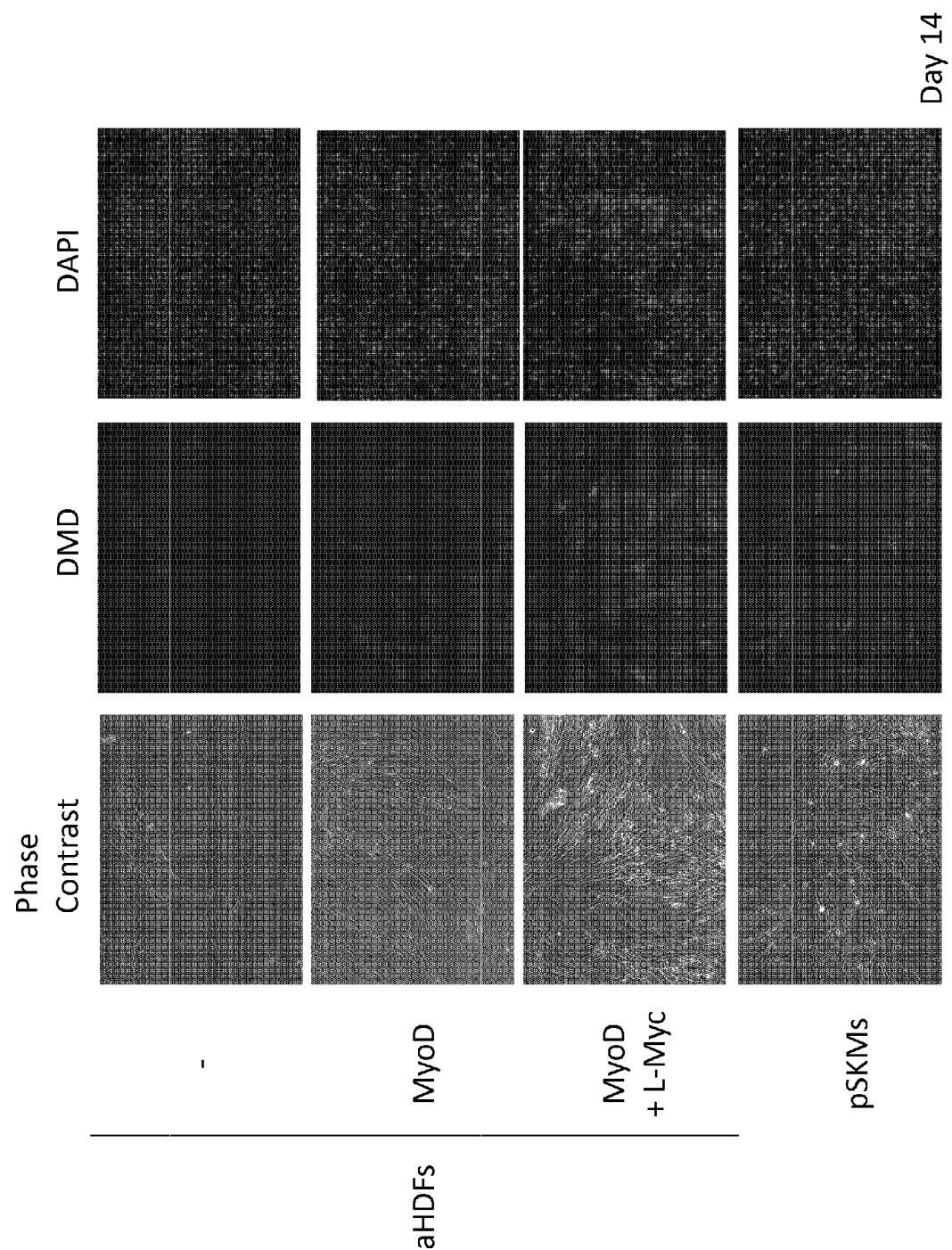
Figure 3:
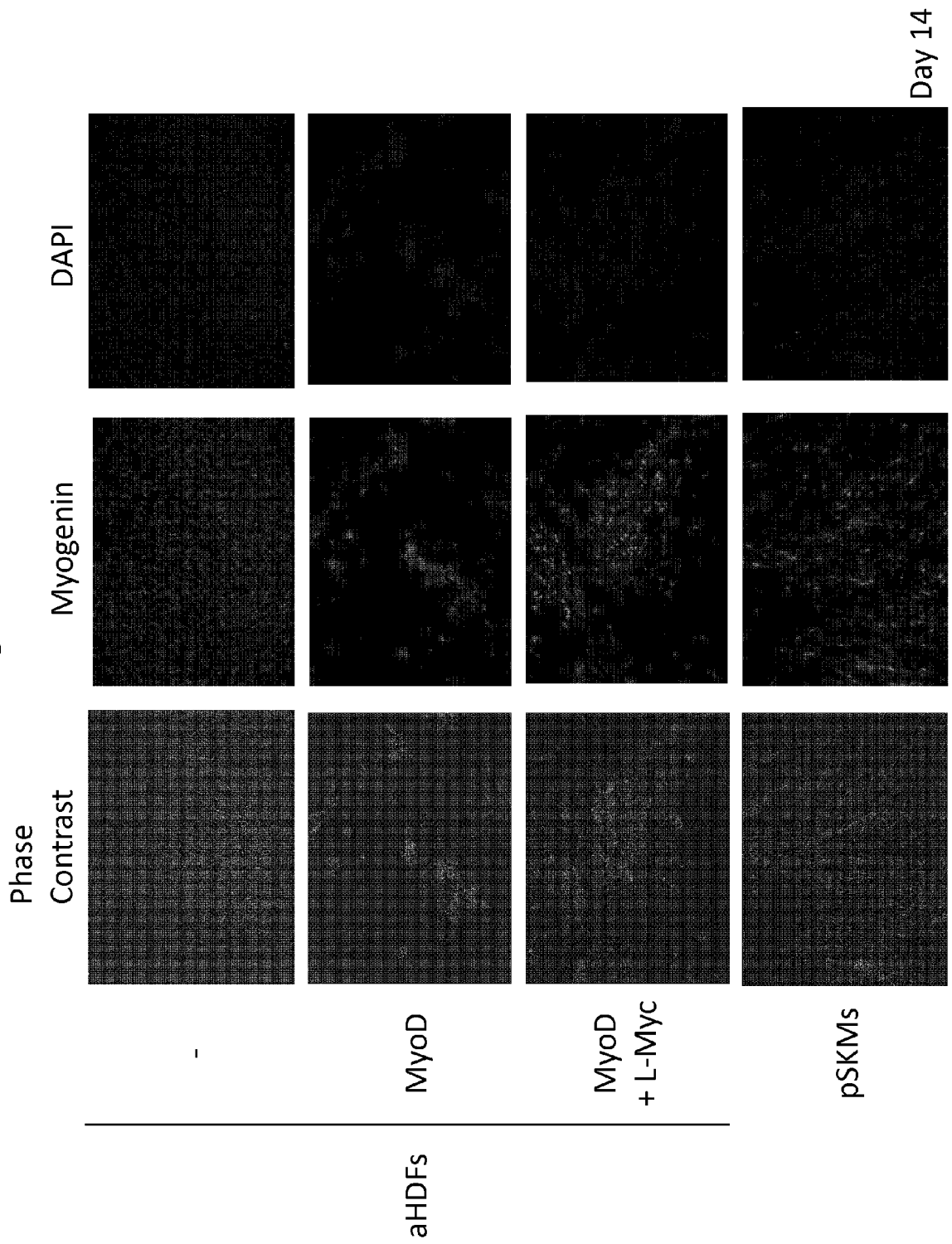

Example 1 (FIG. 1

FIG. 1 shows the outline of the method. cDNA coding sequences of MyoD1, L-Myc, c-Myc, Oct4, Klf4, and SOX2 genes were incorporated into a retrovirus vector plasmid pMXs.puro by using GeneArt Seamless Cloning & Assembly Kit (Thermo Fisher Scientific). Packaging cells, Plat GP cells, were suspended in DMEM medium (normal medium) added with 1% NEAA, 10% FBS and supplemented with 100 U/mL Penicillin and 100 µg/ml Streptomycin, and seeded in a gelatin-coated 10 cm culture dish at $5 \times 10^6$ cells.

After 24 hr culture, the pMXs vector incorporating the above-mentioned genes was introduced at the following ratio in various combinations together with pCMV VSV vector by using X-tremeGENE 9.

That is, a blending solution of transgene 5 µg, pCMV.VSV 2.5 µg, Opti-MEM 500 µl, X-tremeGENE 9 22.5 µl was added to the 10 cm dish containing 10 ml of the medium.

After 24 hours, the medium was changed to a normal medium free of an antibiotic agent. On the same day, aHDF, which is a human normal skin fibroblast strain, was seeded in a 10 cm culture dish at $2.2 \times 10^6$ cells/mL.

After 24 hours, Plat GP culture supernatant was passed through a syringe filter with a pore diameter of 0.45 µm and blended with polybrene (final concentration 4 µg/mL) (virus solution).

The culture supernatant of human normal skin fibroblast (aHDF) was removed by suction and the virus solution was added (Day 0).

After 24 hours of culture and infection, the culture supernatant was removed by suction and myoblast differentiation medium (αMEM medium added with 1% NEAA, 5% Horse Serum and supplemented with IGF-1 10 ng/ml, 100 U/mL Penicillin and 100 µg/ml Streptomycin) was added. Thereafter, the culture medium was exchanged once every two days and the cells were cultured up to Day 14.

Example 2 (FIG. 2 mRNA expression results of Myogenin gene and CKM gene in the conversion of human normal skin fibroblast to myoblast.

Human normal skin fibroblasts (aHDF) were seeded in a 12 well plate and cultured according to the method of FIG. 1.

Human MyoD1 gene, human Oct4 gene, human Sox2 gene, human Klf gene, human L-myc gene, human c-Myc gene were introduced in the indicated combinations.

At 14 days after gene transfer, total RNA was recovered, and cDNA was synthesized using Rever Tra Ace qPCR RT Master Mix. To quantify mRNA levels of Myogenin gene, CKM gene and β actin gene, Real-time PCR Master Mix, Taqman pobe, Specific Primer and cDNA were blended and Real-time RT-PCR was performed using AB7300 Real-time PCR system. The value of Myogenin mRNA and CKM mRNA level to β actin mRNA level in each cell was calculated.

The results are shown in FIG. 2. The cell introduced with two genes of MyoD1 and L-Myc showed the most powerful expression of Myogenin gene and CKM gene, which are skeletal muscle cell-specific markers, at the gene level as compared with the control. Only the group introduced with both genes of human MyoD1 gene and human L-myc gene showed expression equivalent to that of primary human skeletal muscle cell (pSKM).

Example 3 (FIG. 3

Cells were cultured in a 12 well plate and expression of skeletal muscle cell specific markers (Myogenin, CKM, Dystrophin) was confirmed by immunofluorescence staining. Human normal skin fibroblast aHDF was cultured in a 12 well plate and subjected to an experiment as in FIG. 1. At 14 days after gene transfer, the culture medium was removed by suction from each well, and the cells were washed with PBS(−). After fixing with 4% paraformaldehyde, the cells were washed three times with PBS(−), after which Blocking One was added and the mixture was incubated at room temperature for 60 min.

Primary antibodies (anti-CKM antibody, anti-Dystrophin antibody, anti-Myogenin antibody) were reacted overnight at 4° C. and washed 3 times with Wash buffer. Secondary antibodies (Alexa 488-conjugated anti-rabbit IgG antibody, Alexa 546-conjugated anti-mouse IgG antibody) were reacted at room temperature for 1 hr, washed 3 times with Wash buffer, and nuclear staining was performed using SlowFadeGold anti fade reagent with DAPI manufactured by Life Technologies. Images were taken using a fluorescence microscope (Keyence BZ710).

The results are shown in FIGS. 3-1, 3-2, 3-3. CKM, DMD, Myogenin were more powerful and more positive in the cell introduced with MyoD1 and LMyc than in the cell introduced with MyoD1 alone.

In addition, the cell introduced with MyoD1 and LMyc was stained more strongly by CKM, DMD, Myogenin than in primary human myoblast.

Figure 4:
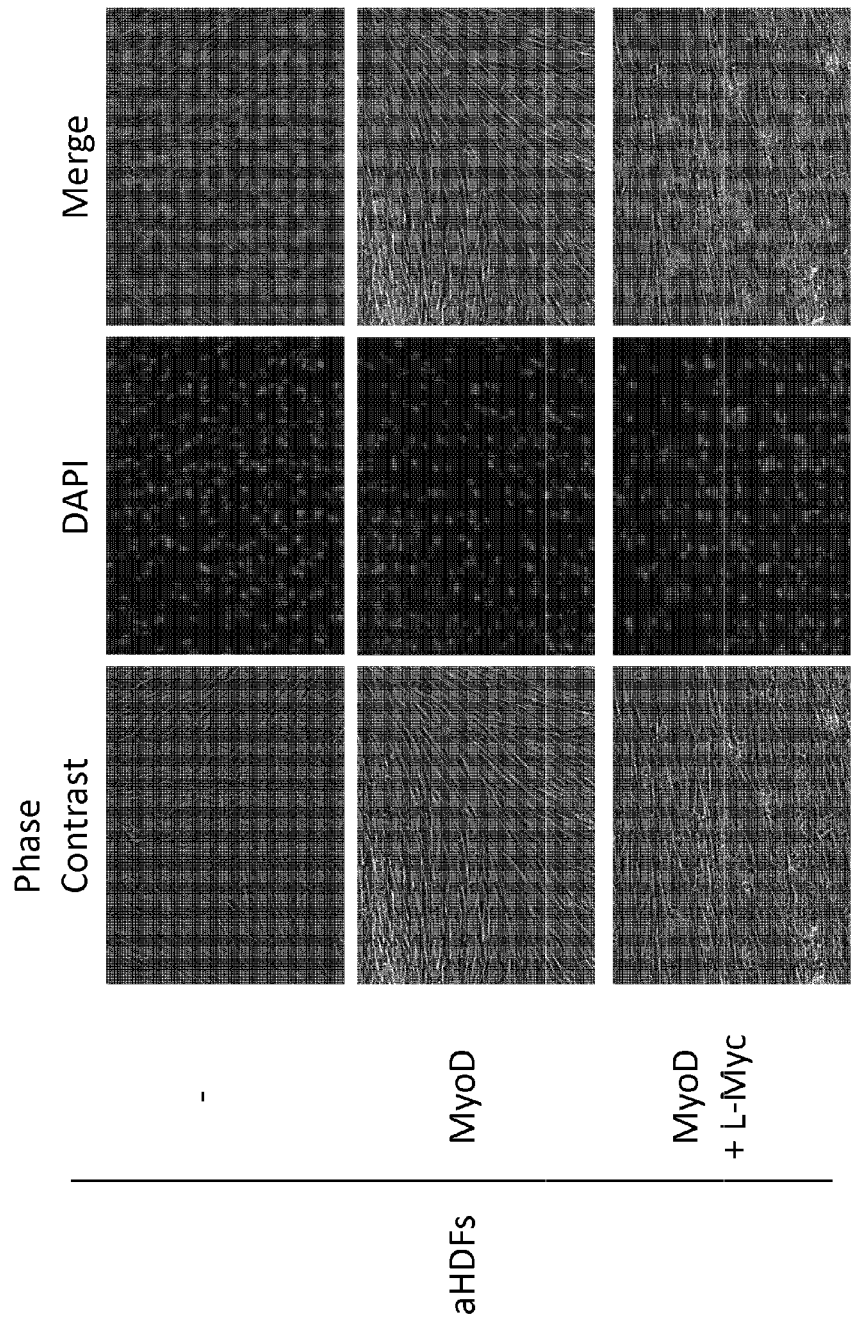
FIG. 4 shows observation results of the emergence of multinucleated myotube cells.

Example 4 (FIG. 4

Cells were cultured in a 12 well plate and emergence of multinucleated myotube cell was observed. Human normal skin fibroblast aHDF was cultured in a 12 well plate and cultured according to the method of FIG. 1. At 14 days after gene transfer, the culture medium was removed by suction from each well, and the cells were washed with PBS(−). After fixing with 4% paraformaldehyde, the cells were washed three times with PBS(−), and nuclear staining was performed using SlowFadeGold anti fade reagent with DAPI manufactured by Life Technologies. Images were taken using a fluorescence microscope (Keyence BZ710). Multinucleated myotube cells were highly frequently observed in the group after co-transfection with MyoD1 and L-Myc. It is clear that cell fusion is promoted by co-transfection of L-Myc or c-Myc gene with MyoD1 gene.

Figure 5:
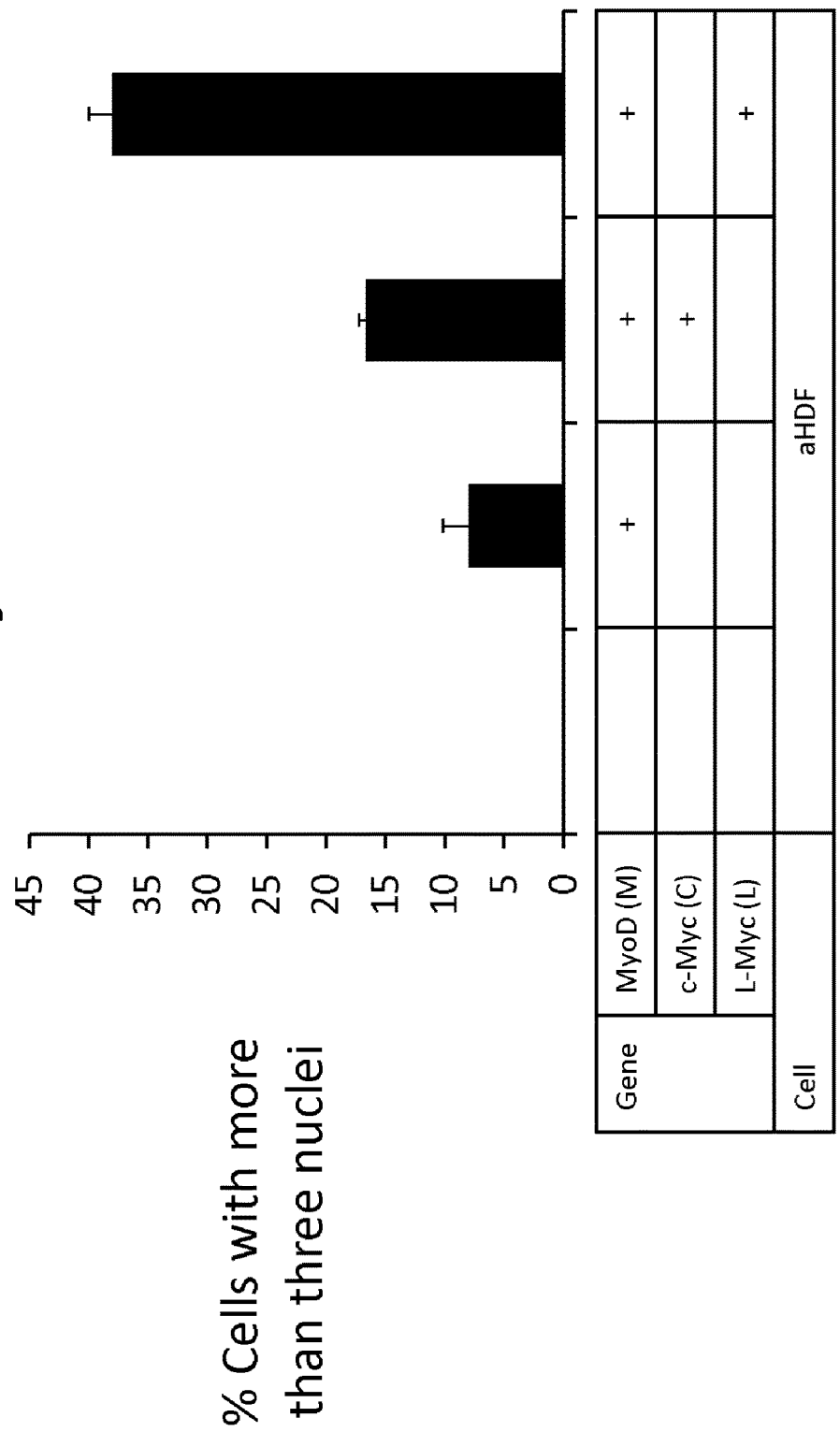
FIG. 5 shows evaluation results of the emergence of multinucleated myotube cells.

Example 5 (FIG. 5

Cells were cultured in a 12 well plate and emergence of multinucleated myotube cell was observed.

Human normal skin fibroblast aHDF was cultured in a 12 well plate and cultured according to the method of FIG. 1. At 14 days after gene transfer, the culture medium was removed by suction from each well, and the cells were washed with PBS(−). After fixing with 4% paraformaldehyde, the cells were washed three times with PBS(−), and nuclear staining was performed using SlowFadeGold anti fade reagent with DAPI manufactured by Life Technologies. The cells were observed under a phase contrast microscope and the cells and nuclei were counted.

The results are shown in FIG. 5. Myotube cells having more than 3 (not less than 4) nuclei highly frequently emerged in the group introduced with MyoD1 and L-Myc.

Figure 6:
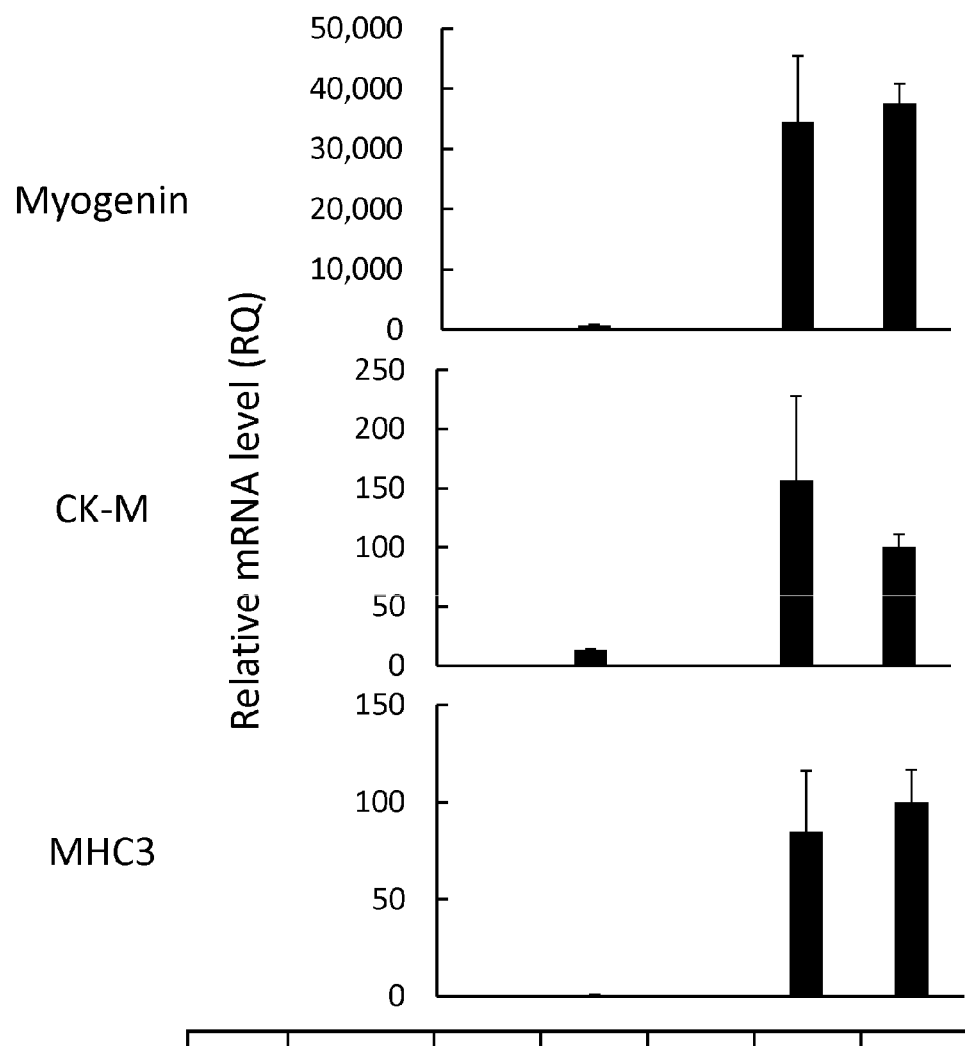
FIG. 6 shows mRNA expression measurement results of Myogenin gene, CKM gene and MHC3 gene.

Example 6 (FIG. 6 mRNA expression results of Myogenin gene, CKM gene and MHC3 gene in the conversion of human normal skin fibroblast to myoblast.

Human normal skin fibroblasts (aHDF) were cultured in a 12 well plate and cultured according to the method of FIG. 1.

Human MyoD1 gene and human L-myc gene were each singly or simultaneously introduced and 14 days later, total RNA was recovered, and cDNA was synthesized using Rever Tra Ace qPCR RT Master Mix. To quantify mRNA levels of Myogenin gene, CKM gene, MHC3 gene and β actin gene, Real-time PCR Master Mix, Taqman pobe, Specific Primer and cDNA were blended and Real-time RT-PCR was performed using AB7300 Real-time PCR system. The values of Myogenin mRNA and CKM mRNA levels to β actin mRNA level in each cell were calculated.

The results are shown in FIG. 6. The cell introduced with two genes of MyoD1 and L-Myc showed, as compared with the control, powerful expression of Myogenin gene, CKM gene and MHC3 gene, which are skeletal muscle cell-specific markers, at the gene level which was equivalent to that of primary skeletal muscle cell (pSKM).

Figure 7:
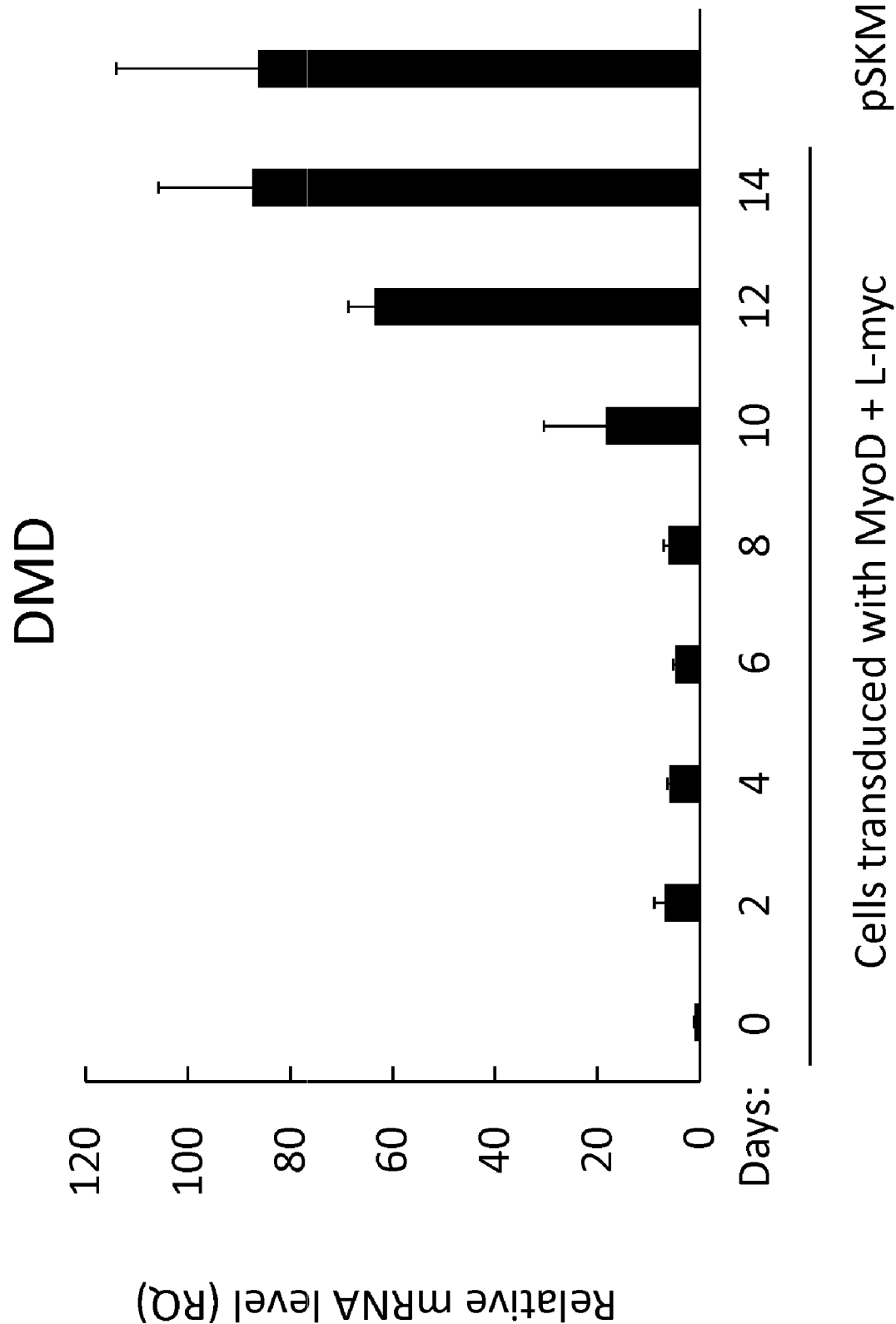
FIG. 7 shows time-course mRNA expression measurement results of DMD gene.

Example 7 (FIG. 7

Time-course mRNA expression results of DMD gene in the conversion of human normal skin fibroblast to myoblast.

Human normal skin fibroblasts (aHDF) were cultured in a 12 well plate and cultured according to the method of FIG. 1.

Human MyoD1 gene and human L-myc gene were co-transfected, and total RNA was recovered on 0, 2, 4, 6, 8, 10, 12, and 14 days after introduction. cDNA was synthesized using Rever Tra Ace qPCR RT Master Mix. To quantify mRNA levels of DMD gene and β actin gene, Real-time PCR Master Mix, Taqman pobe, Specific Primer and cDNA were blended and Real-time RT-PCR was performed using AB7300 Real-time PCR system. The value of DMD mRNA level to β actin mRNA level in each cell was calculated.

The results are shown in FIG. 7. The cell introduced with two genes of MyoD1 and L-Myc showed expression of DMD gene, which is a protein essential for the functional expression of skeletal muscle cells, wherein the expression became stronger over time to be equivalent to that of primary skeletal muscle cells (pSKM) on day 14.

Example 8 (FIG. 8

Cells introduced with MyoD1 and L-Myc were cultured for 7 days and subcutaneously transplanted to the abdomen of mouse by injection. A section was produced from an isolated specimen and immunostaining was performed.

FIG. 8 shows the outline of the method. cDNA coding sequences of MyoD1 and L-Myc genes were incorporated into a retrovirus vector plasmid pMXs.puro by using GeneArt Seamless Cloning & Assembly Kit (Thermo Fisher Scientific). Packaging cells, Plat GP cells, were suspended in DMEM medium (normal medium) added with 1% NEAA 10% FBS and supplemented with 100 U/mL Penicillin and 100 μg/ml Streptomycin, and seeded in a gelatin-coated 10 cm culture dish at $5\times10^6$ cells.

After 24 hr culture, the pMXs vector containing the above-mentioned genes was introduced at the following ratio in various combinations together with pCMV VSV vector by using X-tremeGENE 9.

That is, a blending solution of transgene 5 μg, pCMV.VSV 2.5 μg, Opti-MEM 500 μl, X-tremeGENE 9 22.5 μl was added to the 10 cm dish containing 10 ml of the medium.

After 24 hours, the medium was changed to a normal medium free of an antibiotic agent. On the same day, aHDF, which is a human normal skin fibroblast strain, was seeded in a 10 cm culture dish at $2.2\times10^6$ cells/mL.

After 24 hours, Plat GP culture supernatant was passed through a syringe filter with a pore diameter of 0.45 μm and blended with polybrene (final concentration 4 μg/mL) (virus solution).

The culture supernatant of aHDF was removed by suction and the virus solution was added (Day 0).

After 24 hours of culture and infection, the culture supernatant was removed by suction and myoblast differentiation medium (αMEM medium added with 1% NEAA, 5% Horse Serum and supplemented with IGF-1 10 ng/ml, 100 U/mL Penicillin and 100 μg/ml Streptomycin) was added. Thereafter, the culture medium was exchanged once every two days and the cells were cultured 30 up to Day 7.

On Day 7, the cells were detached from the dish using Accutase and dissolved in 100 μL of Matrigel (CORNING REF354234) stock solution by $3\times10^5$ cells on ice.

The cell solution suspended in Matrigel was subcutaneously transplanted into the right upper abdomen of the NOD/SCID mouse by injection. aHDF dissolved in 100 μL of Matrigel (CORNING REF354234) stock solution on ice by $3\times10^5$ cells was transplanted by injection. One week after transplantation by injection, the mice were euthanized, the upper abdominal skin was detached, and the subcutaneous transplanted tissue was removed together with the skin.

Figure 8B:
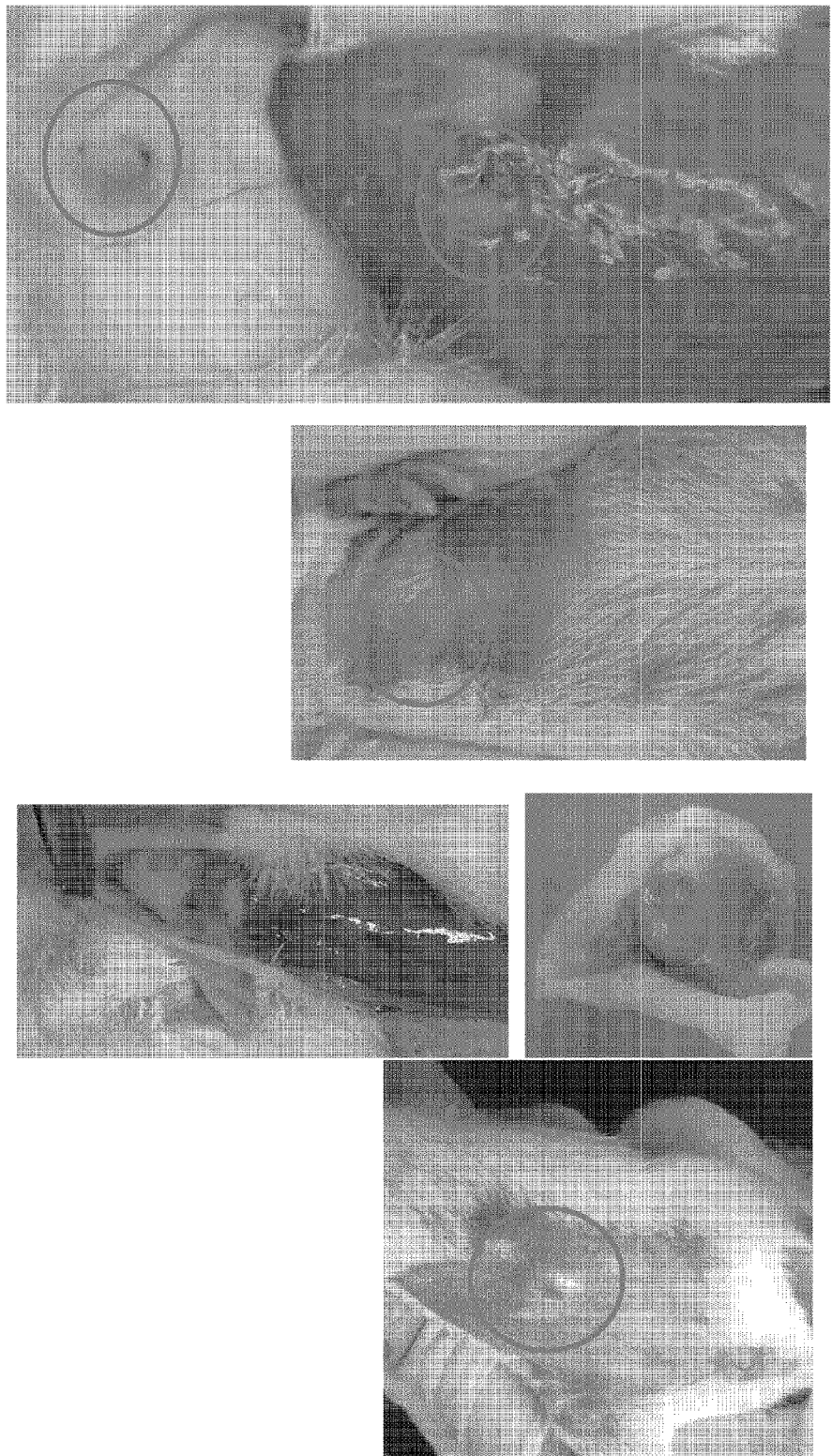
FIG. 8B shows macroscopic images of the transplanted site and excised tissue one week after transplantation.

Macroscopic images of the transplantation site and the excised tissue one week after transplantation are shown in FIG. 8B. Fibrous nodular tissue was observed at the transplantation site of the cells introduced with MyoD1 and L-Myc genes.

Figure 9:
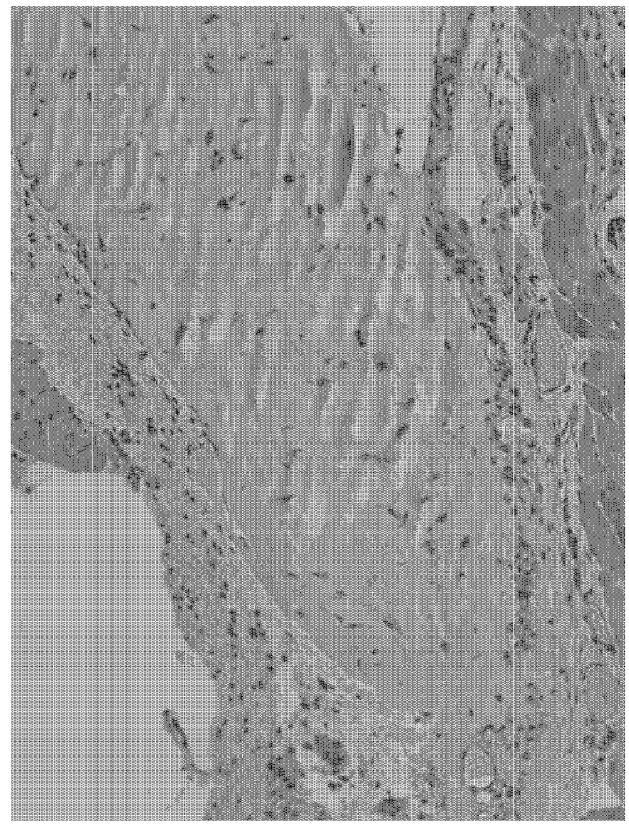
Figure 1:
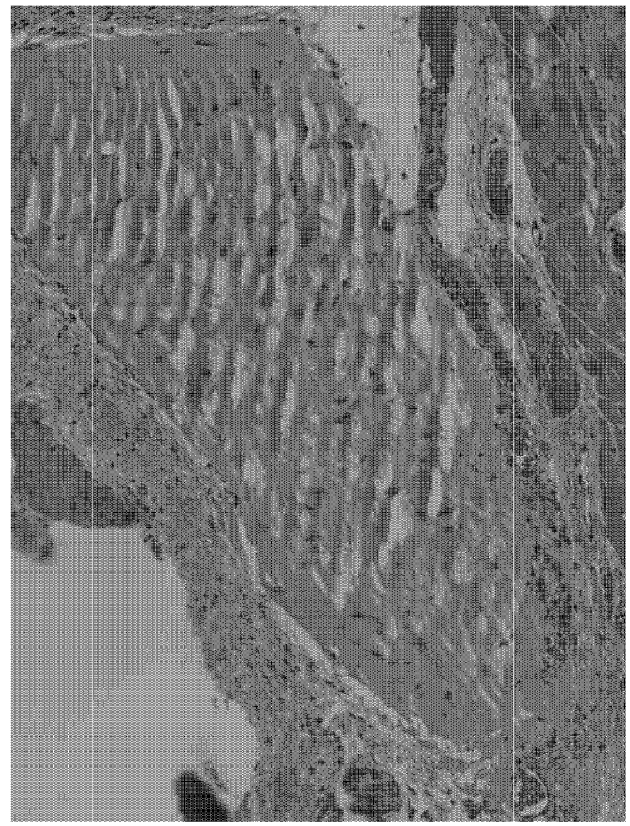
FIG. 1 shows the outline of an experiment method.
Figures 2, 9:
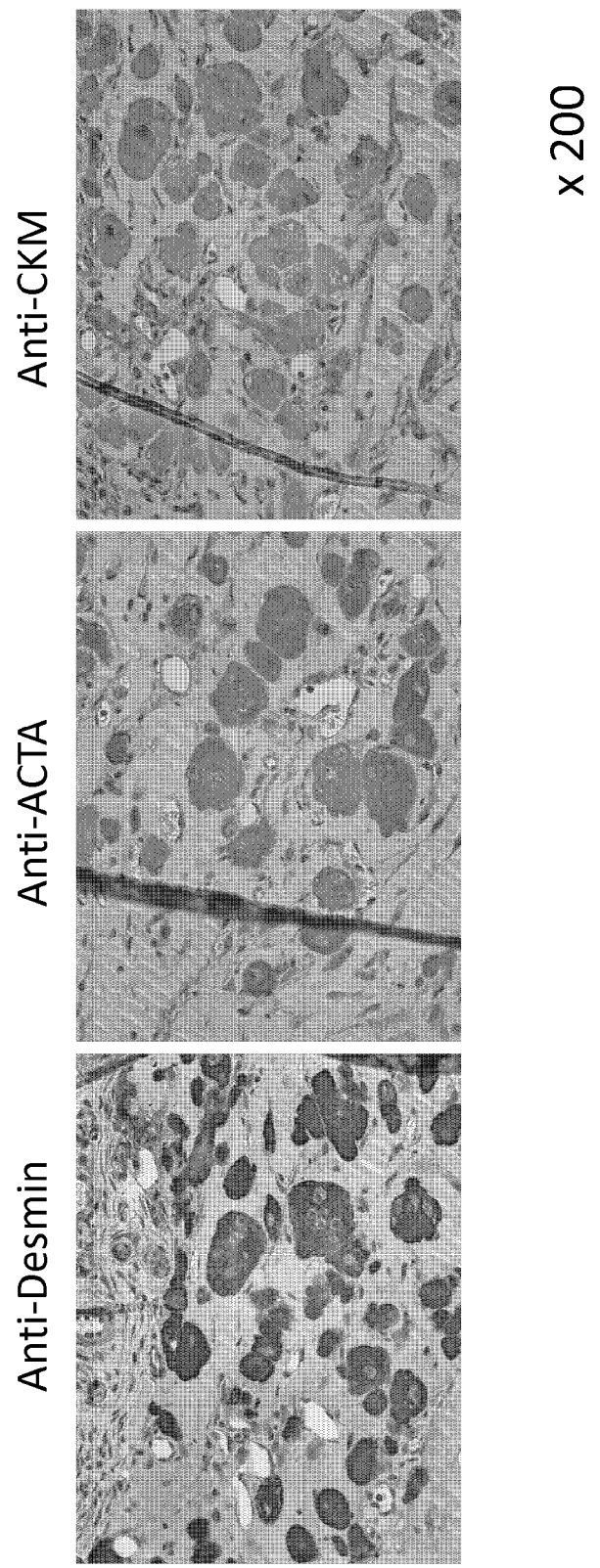

Example 9 (FIG. 9

The tissue excised in Example 8 was fixed with 4% paraformaldehyde for 24 hr. Thereafter, embedded in paraffin over 24 hr to prepare a paraffin block.

A slice section with 3 μm thickness was produced from the paraffin-fixed mouse subcutaneous tissue specimen. The section was incubated at 60° C. for 15 min and immersed in xylene for 5 min. This was repeated 3 times. It was further immersed in 100% ethanol for 3 min and this was repeated 3 times. Thereafter, the section was deparaffinized and washed with distilled water for 5 min.

Then, BLOXALL was added dropwise to cover the section and the section was stood for 10 min at room temperature.

After washing with PBS for 5 min, 2.5% horse serum was added dropwise to cover the section and the section was stood for 20 min at room temperature.

The slide was lightly knocked against a paper towel to remove serum. As a primary antibody, Desmin antibody, anti-CKM antibody, anti-Dystrophin antibody, anti-ACTA antibody or anti-Myogenin antibody was added dropwise to cover the section. The section was stood for 30 min at room temperature and washed with PBS for 5 min. The slide was lightly knocked against a paper towel to remove PBS.

ImmPRESS reagent was added dropwise to cover the section. The section was stood for 30 min and washed with PBS for 5 min, and the washing was performed twice. The slide was lightly knocked against a paper towel to remove PBS.

ImmPACT DAB Diluent (1 ml) was charged, one drop of ImmPACT DAB Chromogen Concentrate was added and they were mixed well in a Vortex. An enzyme substrate solution was added dropwise to cover the section, and the section was stood for 30 min to 1 min and washed with distilled water for 5 min.

The section was further washed twice with distilled water for 5 min, and nuclear staining was performed with hematoxylin for 5 min. After washing for 5 min with running water, the section was immersed in a water bath at 50° C. for 2 min and washed with running water for 2 min. Immersion in 100% ethanol for 3 min was performed 3 times, and immersion in xylene for 5 min was performed 3 times for dehydration. An encapsulation agent was added dropwise to cover the section and the section was covered with cover glass.

The tissue was observed with Keyence BZ710 in a bright field.

The results are shown in FIG. 9.

In the tissue transplanted with fibroblasts, a myofiber-like structure was not observed in the subcutaneous tissue, a multinucleated cell was not observed, and a Desmin-positive cell was not observed (FIG. 9-1). On the other hand, in the tissue transplanted with the cells introduced with MyoD1 and L-Myc, a myofiber-like structure was observed in the subcutaneous tissue, in which many Desmin positive, CKM positive, ACTA positive multinucleated cells could be confirmed (FIG. 9-2). From these results, it could be confirmed that a cell induced by MyoD1 and L-myc gene is engrafted in vivo after transplantation and forms a myofiber-like tissue.

Example 10

In the same manner as in Examples 8 and 9, human fibroblasts (aHDFs) without gene transfer or cells infected with a retrovirus vector incorporating MyoD1 gene and a retrovirus vector incorporating L-myc gene and cultured for 7 days (dMBs (directly converted myoblasts)) were mixed with Matrigel (BD Bioscience, San Jose, Calif.) at a volume ratio of 1:1, and transplanted into the side abdomen of NOG/SCID mouse (cell number was $3\text{-}5 \times 10^5$ cells/mouse). Seven days later, a tissue at the transplantation site was isolated and, in the same manner as in Example 9, fixed with 4% paraformaldehyde for 8 h, embedded in paraffin and sliced. Immunohistochemistry was performed using anti-desmin antibody, observed under a fluorescence microscope (Keyence BZ710) at ×400 magnification, and the percentage of desmin positive cells per one field was calculated.

Figure 10:
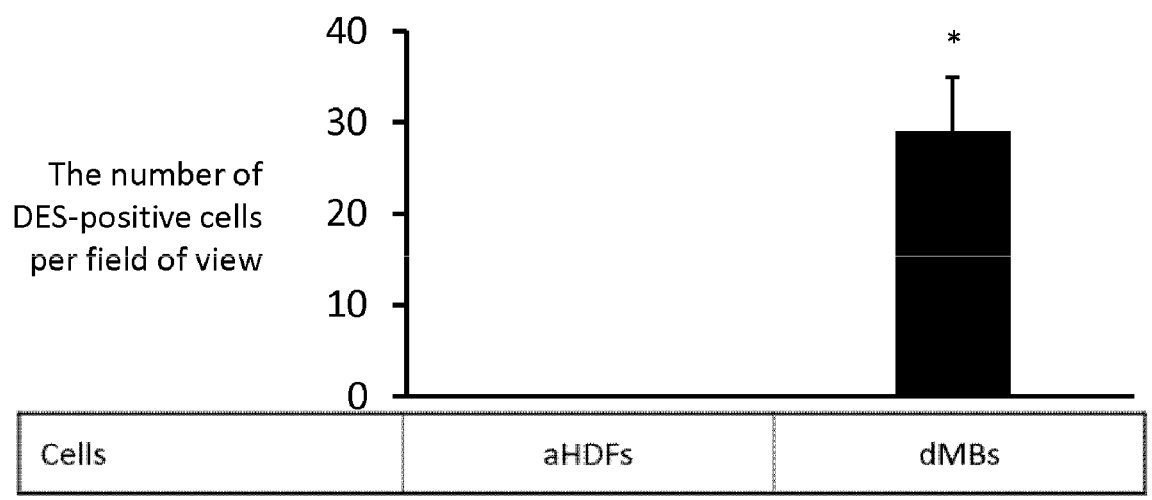
FIG. 10 shows the measurement results of desmin positive cells. The values are average value±standard deviation. Each group N=3 mice. *$P<0.05$ vs non-introduced cells transplantation group.

The results are shown in FIG. 10. It is clear that a significantly large number of desmin-positive cells were present in the tissue at the transplantation site in the group transplanted with ML-introduced cells (dMBs (directly converted myoblasts)). The values are average value±standard deviation. Each group N=3 mice. *P<0.05 vs non-introduced cell transplantation group.

Example 11

In the same manner as in Example 1, human fibroblasts were infected with a retrovirus vector incorporating MyoD1 gene (M). Other cells were infected with both retrovirus vector incorporating L-myc gene (L) and retrovirus vector incorporating MyoD1 gene (M) (ML). As a control, cells free of infection with a retrovirus vector were also prepared (−). These were cultured in a myoblast differentiation medium in the same manner as in Example 1. 14 days after infection, immunofluorescent staining using anti-CKM antibody and nuclear staining were performed in the same manner as in Example 3. Images were taken using a fluorescence microscope (Keyence BZ710), and the percentage of CKM positive cells to the total cell number was counted.

Figure 11:
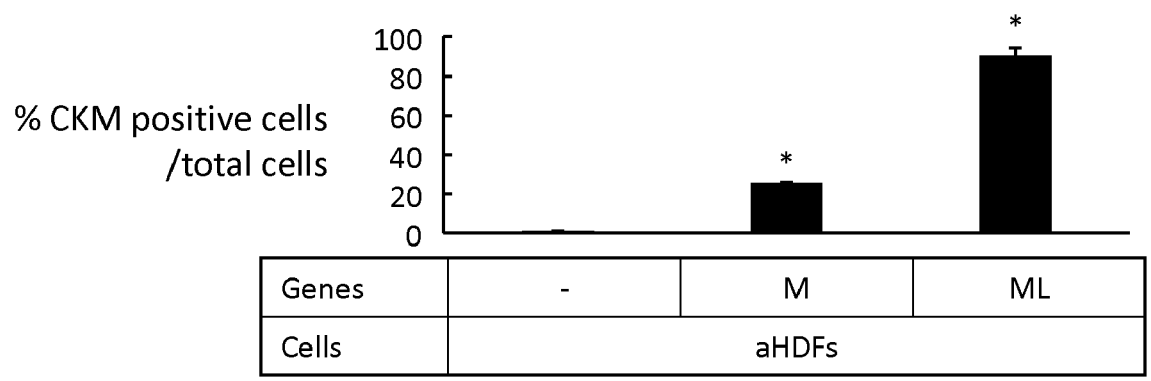
FIG. 11 shows the measurement results of CKM positive cells. The values are average value±standard deviation. Each group N=3 wells. *$P<0.05$ vs non-introduced cells.

The results are shown in FIG. 11. About 26% of the cells introduced with MyoD1 gene alone were CKM positive, whereas about 90% of the cells co-introduced with MyoD1 gene and L-myc gene were CKM positive. Therefore, it was found that about 90% of human fibroblasts are converted to myoblasts by co-introduction with MyoD1 and L-myc genes. The values are average value±standard deviation. N=3 wells/group. *P<0.05 vs non-introduced cells.

Example 12

In the same manner as in Example 1, human fibroblasts were infected with a retrovirus vector incorporating MyoD1 gene (M), retrovirus vector incorporating L-myc gene (L) and retrovirus vector incorporating c-Myc gene (C) in the described combination. As a control, cells free of infection with a retrovirus vector were also prepared (−). These were cultured in a myoblast differentiation medium in the same manner as in Example 1. 14 days after infection, nuclear staining was performed in the same manner as in Example 3. Images were taken using a fluorescence microscope (Keyence BZ710) (FIG. 12A). In addition, the percentage of cells having more than 3 nuclei was counted (FIG. 12B).

About 6% of the cells introduced with MyoD1 gene alone were cells having more than 3 nuclei, whereas about 43% of the cells co-introduced with MyoD1 gene and L-myc gene were cells having more than 3 nuclei. About 27% of the cells co-introduced with MyoD1 gene and c-Myc gene were cells having more than 3 nuclei. Therefore, it was found that the cells co-introduced with MyoD1 gene and L-myc gene become multinucleated cells with the highest efficiency. The values of FIG. 12B are average value±standard deviation. Each group N=3 wells. *P<0.05 vs non-introduced cells.

Example 13

Figure 13:
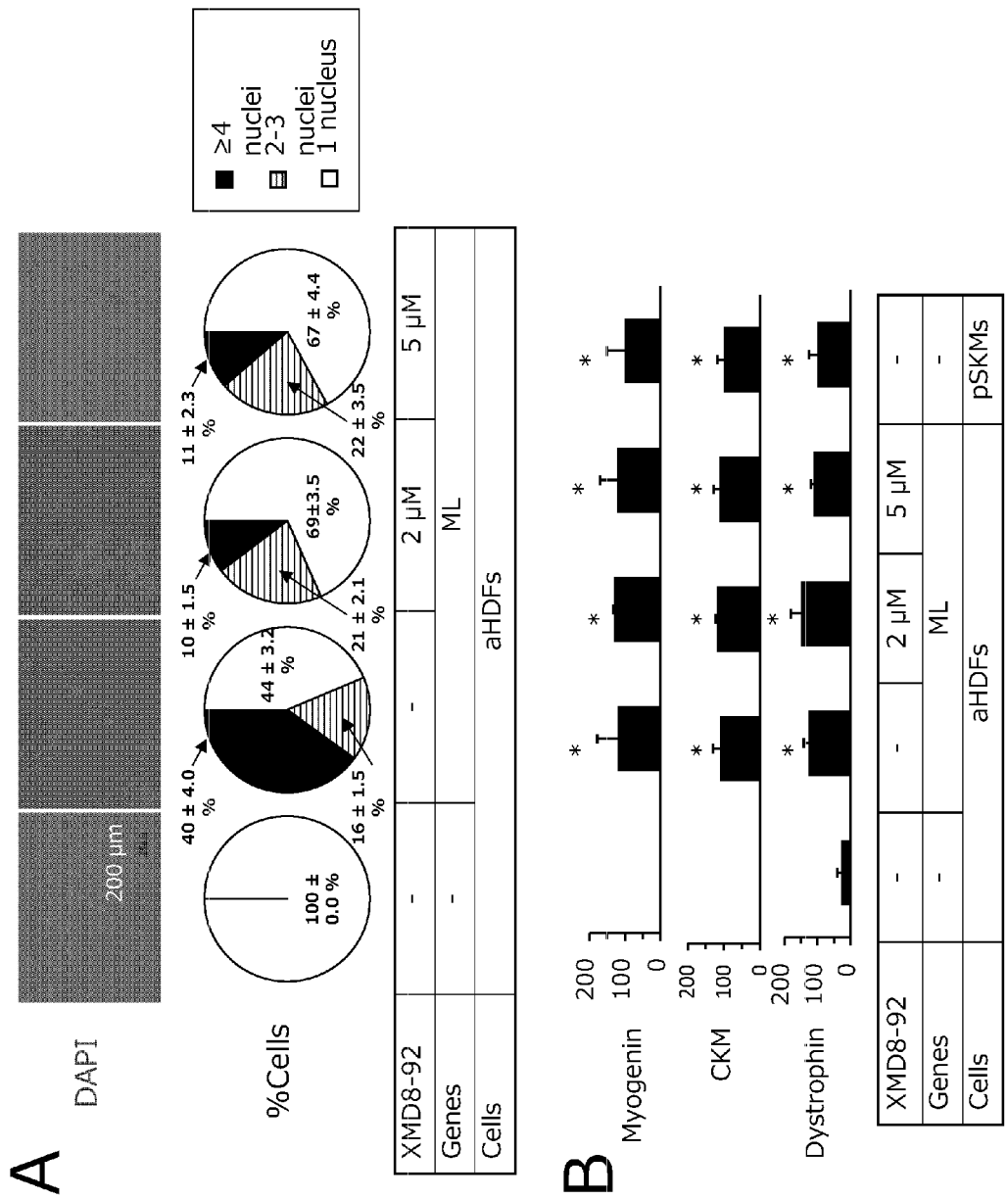
FIG. 13 (A) shows the measurement results of emergence of multinuclear cell. (B) shows the mRNA expression measurement results of Myogenin gene, CKM gene and Dystrophin gene.

In the same manner as in Example 12, human fibroblasts were infected with both a retrovirus vector incorporating MyoD1 gene and a retrovirus vector incorporating L-myc gene (ML). As a control, cells free of infection with a retrovirus vector were also prepared (−). A ERK5 pathway inhibitor, XMDB-92, was added at the indicated concentration to some groups. These were cultured in a myoblast differentiation medium in the same manner as in Example 12. 14 days after infection, nuclear staining was performed in the same manner as in Example 3. Images taken using a fluorescence microscope (Keyence BZ710) are shown (FIG. 13A, upper panel). In addition, the percentages of cells having 4 or more nuclei, cells having 2-3 nuclei and cells having one nucleus were calculated (FIG. 13A, lower panel).

The fibroblasts without gene transfer were all mononuclear cells, about 40% of the cells infected with ML were cells having not less than 4 nuclei, and about 16% were cells having 2-3 nuclei. However, addition of 2-5 µM XMD8-92, which is an ERK5 inhibitor, decreased the cells having not less than 4 nuclei to about 10-12%, and the cells having 2-3 nuclei to about 21-23%.

In addition, 14 days after infection, RNA was extracted from the cells. As a control, RNA was also extracted from the primary human skeletal muscle cells (pSKMs). mRNAs of Myogenin, CKM, Dystrophin were quantified by real time RT-PCR. The results are shown in FIG. 13B. The induction of expression of these myoblast specific genes by ML gene transfer was not suppressed by the addition of XMD8-92. Therefore, it was found that suppression of multinucleation by ERK5 pathway inhibition is not suppression of conversion to myoblasts.

From these results, it was found that multinucleation of cells by co-introduction with MyoD1 gene and L-myc gene is caused by ERK5 pathway dependent cell fusion.

Example 14

After experiments in the same manner as in Examples 8, 9, tissue sections of the transplantation site were subjected to immunohistochemistry respectively using anti-CKM antibody and anti-α actin antibody by a method similar to that in Example 10.

Figure 14:
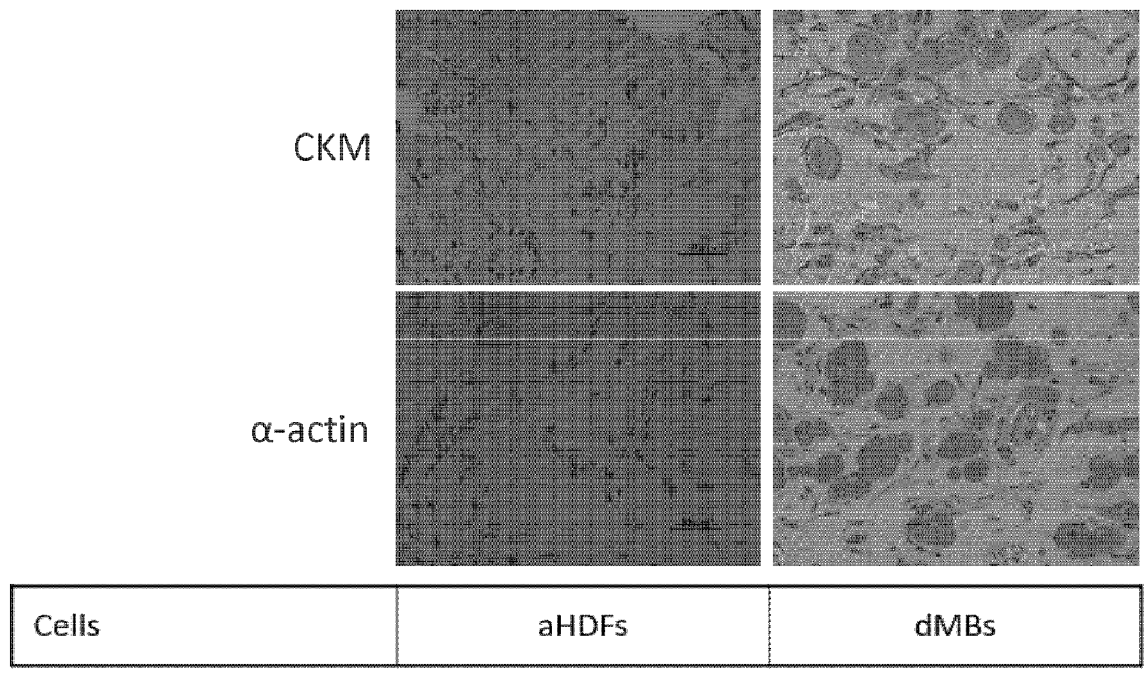
FIG. 14 shows the results of immunohistochemical staining of tissues transplanted with cells.

The results are shown in FIG. 14. It is clear that many CKM- and α actin-positive myofiber-like tissues were formed in the transplantation sites in a group transplanted with the cells co-introduced with MyoD1 gene and L-myc gene (dMBs (directly converted myoblasts)).

Example 15

In the same manner as in Example 1, human fibroblasts were infected with both a retrovirus vector incorporating MyoD1 gene and a retrovirus vector incorporating L-myc gene (ML) and cultured for 10 days in a myoblast differentiation medium. As a control, human fibroblasts free of gene transfer were also used (−). The mRNA expression of UCP1 gene and CIDEA gene, which are brown adipocyte markers, SOX9 gene and aggrecan gene, which are chondrocyte markers, and Runx2 gene and osteocalcin gene, which are osteoblast markers, was measured by real time RT-PCR.

Figure 15:
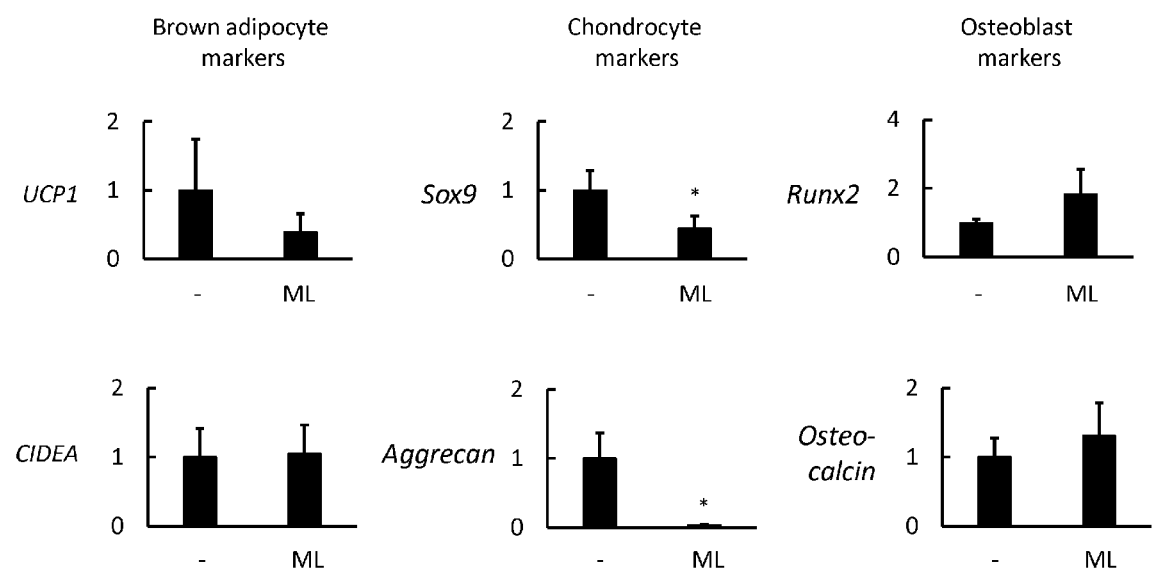
FIG. 15 shows the mRNA expression measurement results of various marker genes. The values are average value±standard deviation. Each group N=3. *$P<0.05$ vs non-introduced cell.

The results are shown in FIG. 15. It is clear that the cells co-introduced with MyoD1 gene and L-myc gene (ML-introduced cells) do not significantly increase expression of any of these mesenchymal cell markers. The values are average value±standard deviation. Each group N=3. *P<0.05 vs. non-introduced cells.

Example 16

In the same manner as in Example 1, human fibroblasts were infected with a retrovirus vector incorporating MyoD1 gene (M), retrovirus vector incorporating L-myc (L) and retrovirus vector incorporating c-Myc (C) in the combinations of M alone, MC and ML indicated in the Figure. As a control, cells free of infection with a retrovirus vector were also prepared (−). These were cultured in a myoblast differentiation medium in the same manner as in Example 1. 14 days after infection, the cells were stained with 200 nM MitoTracker Red probe (Invitrogen) at 37° C. for 15 min. Images were taken using a fluorescence microscope (Keyence BZ710).

Figure 16:
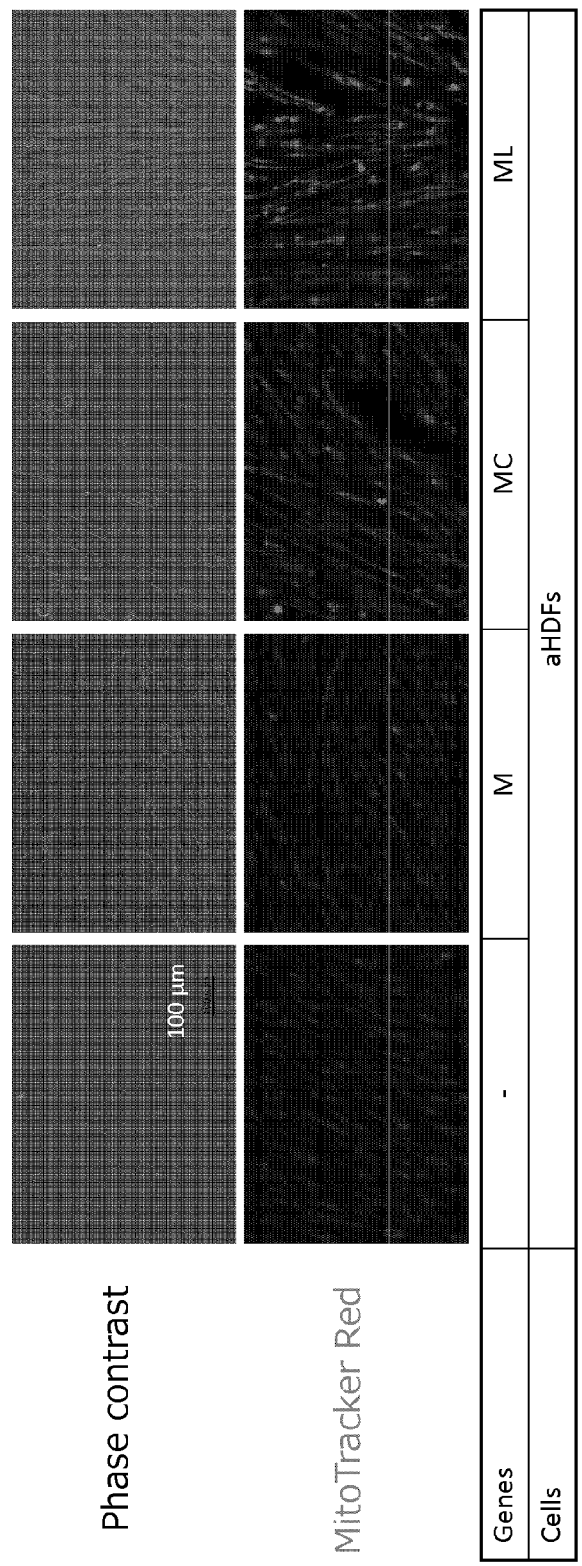
FIG. 16 shows the detection results of mitochondria (MitoTracker Red).

The results are shown in FIG. 16. The upper photographs show phase difference images and the lower photographs are fluorescence images. The cells co-introduced with MC had many mitochondria compared with human fibroblast without gene transfer and the cells introduced with MyoD1 gene alone, and the cells cointroduced with ML had even more mitochondria.

Example 17

Human fibroblasts were infected with both a retrovirus vector incorporating MyoD1 gene and a retrovirus vector incorporating L-myc gene and cultured for 6 days. (ML) As a control, human fibroblasts free of gene transfer were also used (−). Immunostaining with anti-desmin antibody or anti-CKM antibody and nuclear staining with DAPI were performed as described.

The results are shown in FIG. 17. The upper photographs show phase difference images and the lower photographs are fluorescence images. It is clear that ML-introduced cells express myoblast-specific genes Desmin and CKM even after a comparatively short period of culture of 6 days after gene transfer.

Example 18

In the same manner as in Example 1, human fibroblasts were infected with a retrovirus vector incorporating MyoD1 gene (M). They were also infected with both retrovirus vector incorporating L-myc gene (L) and retrovirus vector incorporating MyoD1 gene (ML). These were cultured in a myoblast differentiation medium and RNA was extracted from each cell on day 14 after infection. As a control, RNA was also extracted from the cells (−) without infection with retrovirus vector and primary human skeletal muscle cells (pSKMS). These RNAs were subjected to DNA microarray analysis using GeneChip human Gene 1.0 ST (Affymetrix).

Figure 18A:
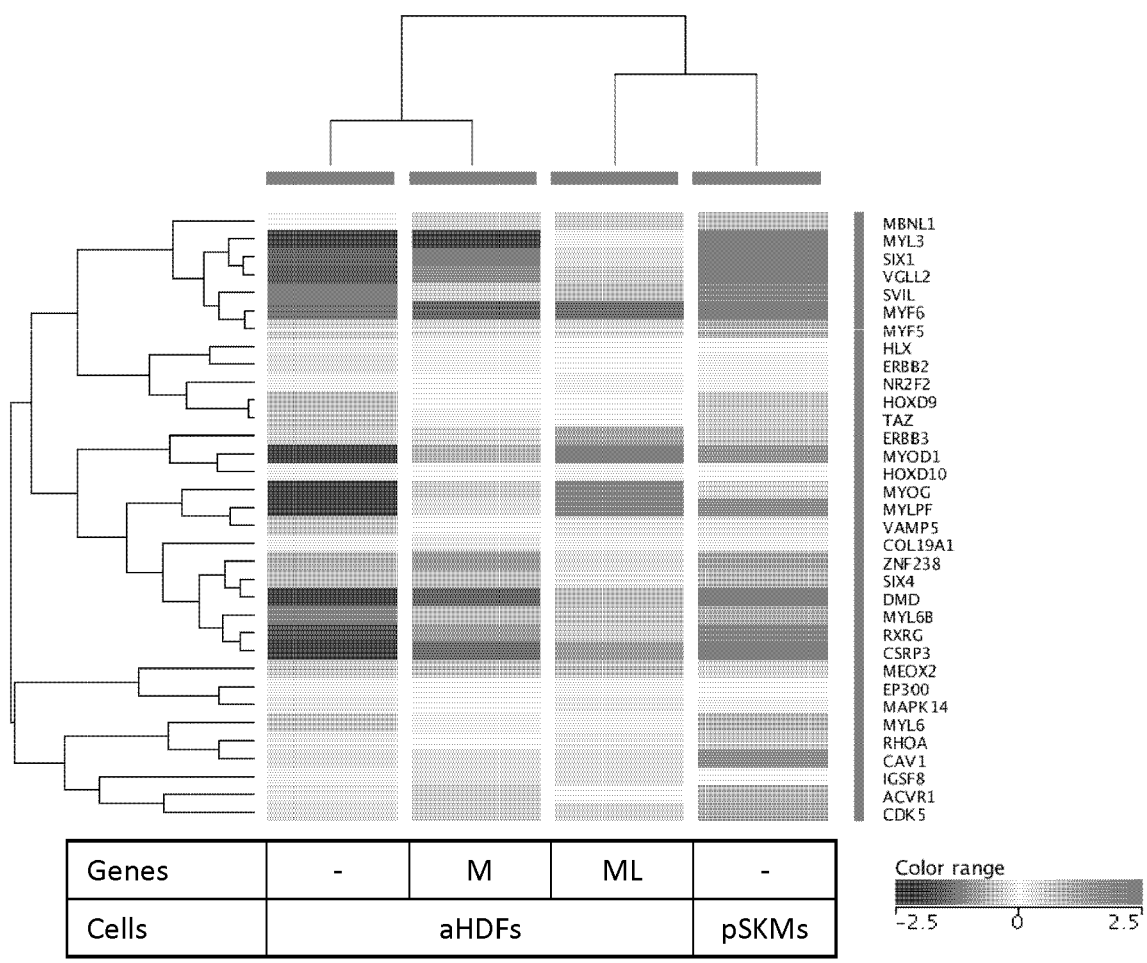
FIG. 18A shows a heatmap and the results of clustering analysis of a gene group involved in the development of skeletal muscle.
Figure 18B:
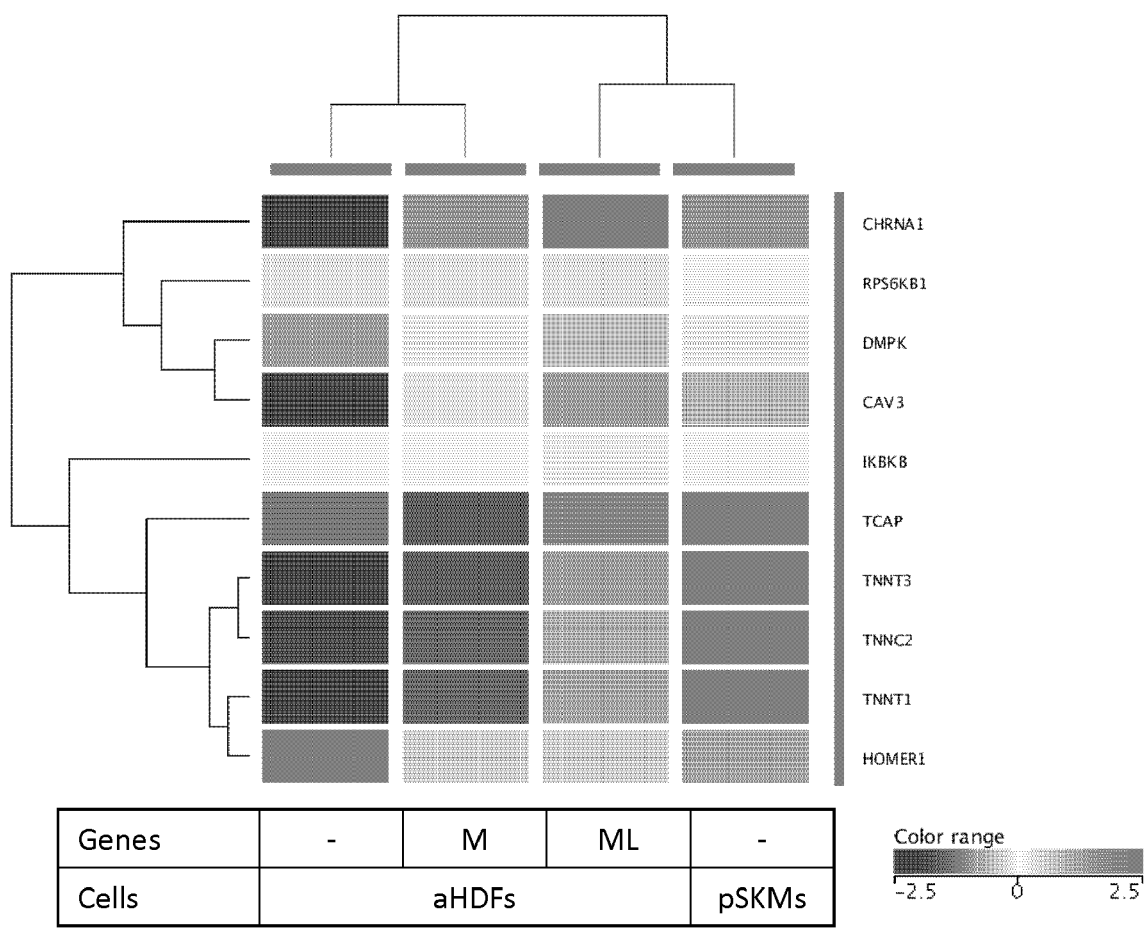
FIG. 18B shows a heatmap and the results of clustering analysis of a gene group involved in the contraction of skeletal muscle.
Figure 18C:
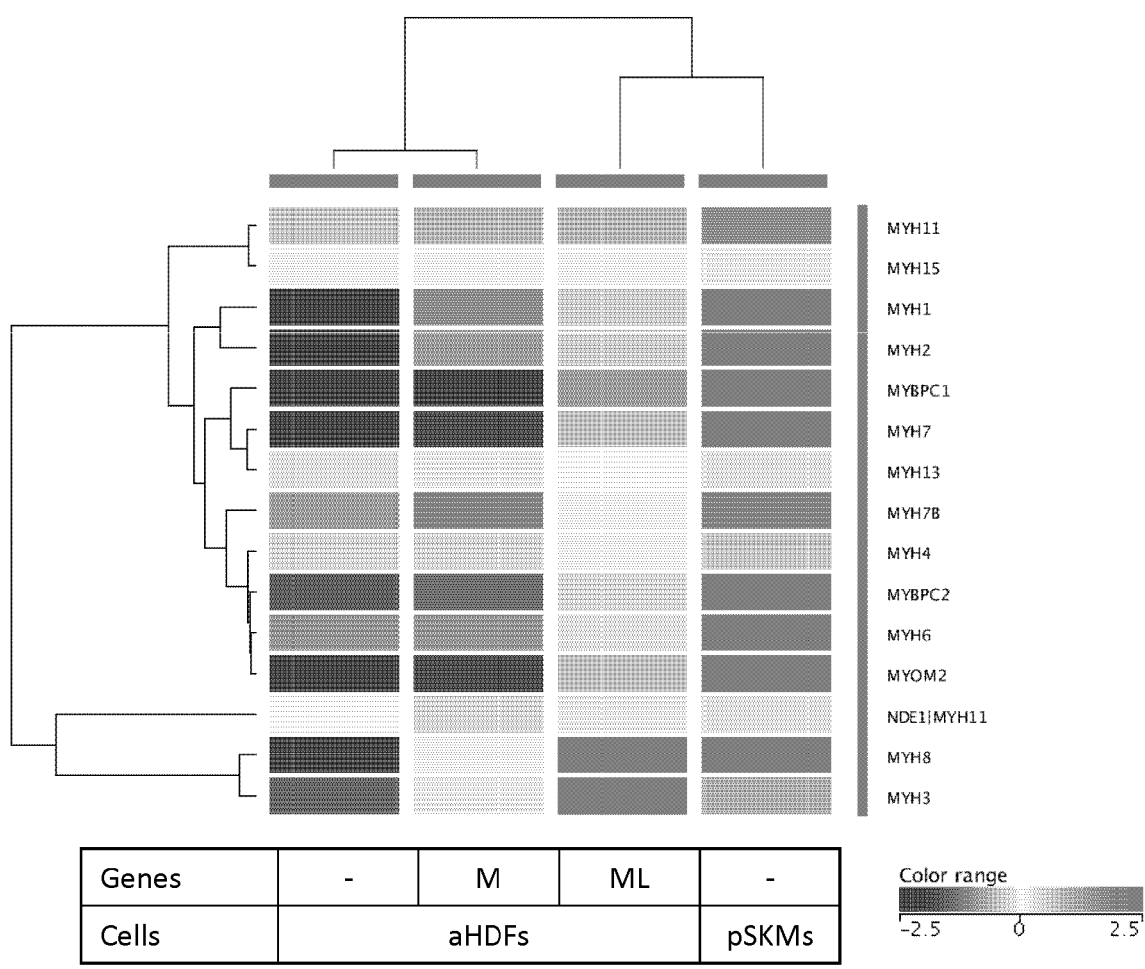
FIG. 18C shows a heatmap and the results of clustering analysis of a gene group relating to myosin filament.
Figure 18D:
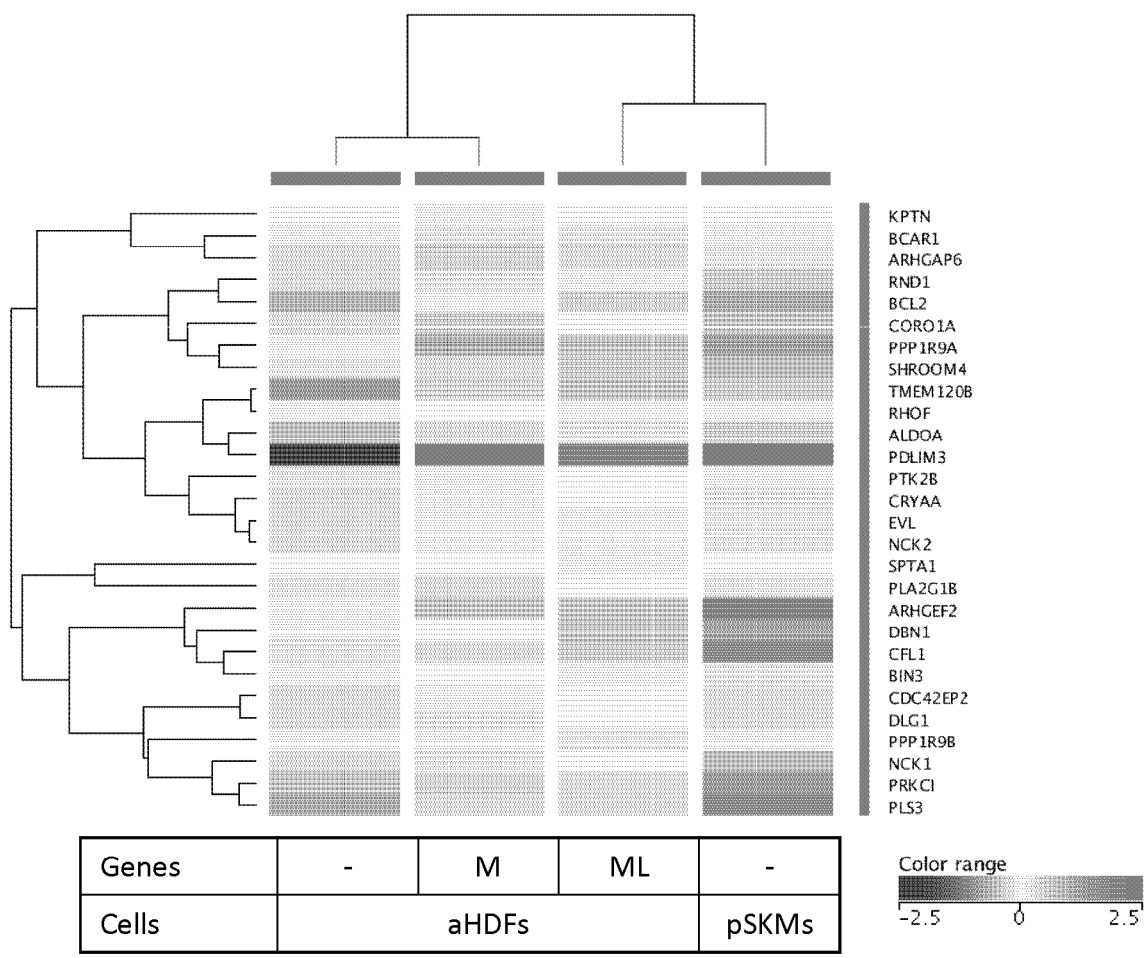
FIG. 18D shows a heatmap and the results of clustering analysis of a gene group relating to actin filament.

The heatmap and clustering analysis results of each of the gene group involved in the development of skeletal muscle (FIG. 18A), the gene group involved in the contraction of skeletal muscle (FIG. 18B), the gene group relating to myosin filament (FIG. 18C), and the gene group relating to actin filament (FIG. 18D) are shown. The expression of all these gene groups relating to skeletal muscle in ML-introduced cells showed the highest homology with pSKMS and low homology with fibroblasts. M single-introduced cells showed higher homology to fibroblasts than to pSKMS.

Example 19

In the same manner as in Example 1, human fibroblasts were infected with both a retrovirus vector incorporating MyoD1 gene and a retrovirus vector incorporating L-myc gene (ML) and cultured in a myoblast differentiation medium. The cells were stained with rBC2LCN-FITC (Wako 180-02991) every two days after infection, and the nucleus was stained with Hoechst33342. As a control, the cells before infection with a retrovirus vector (leftmost) were similarly stained. As a positive control, human iPS cells (hiPS235G1) were also stained similarly. Images of these cells were taken using a fluorescence microscope (Keyence BZ710).

Figure 19:
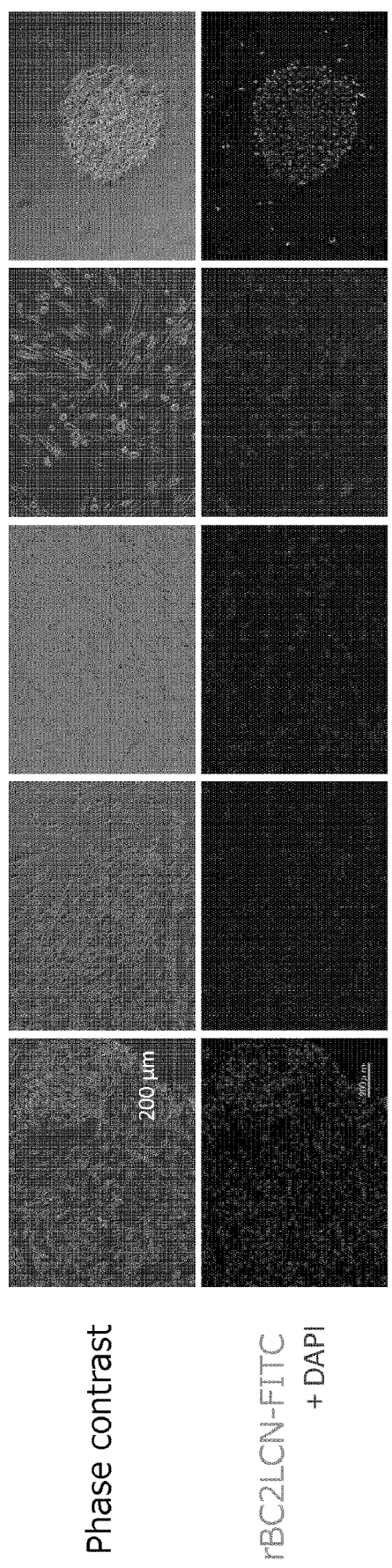
FIG. 19 shows the results of staining of rBC2 LCN-FITC.
Figure 20:
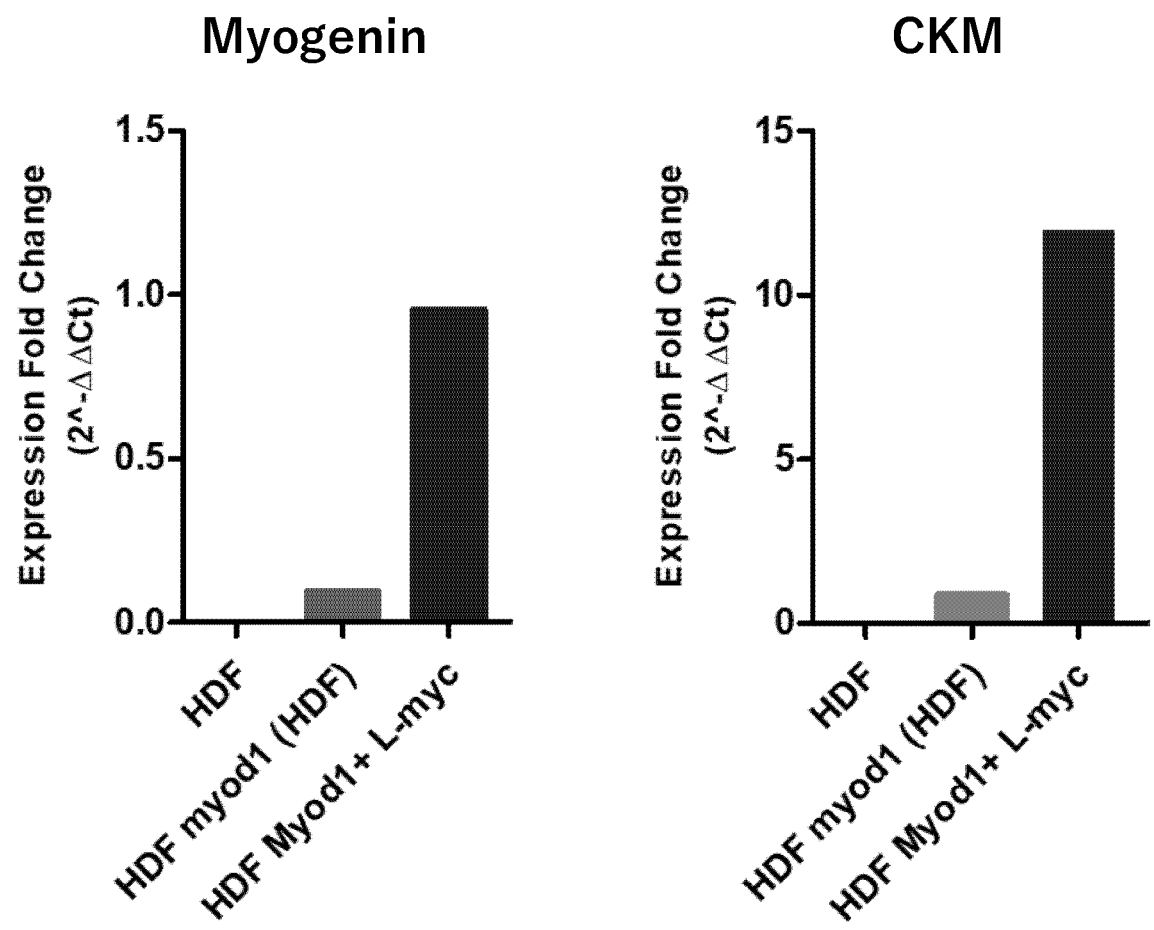
FIG. 20 shows the mRNA expression measurement results of Myogenin gene and CKM gene.

The results are shown in FIG. 19. The upper photographs show phase difference images and the lower photographs are fluorescence images. Fibroblasts are not stained with rBC2LCN-FITC even when infected with ML. It is clear that conversion of fibroblasts to myoblasts by ML gene introduction does not go through iPS cell-like stem cells.

Example 20

MyoD1 gene and L-myc gene were respectively introduced into plasmid vector pCX to construct expression vectors. MyoD1 plasmid alone, or both MyoD1 plasmid and L-Myc plasmid, were introduced into human fibroblasts (HDFs) by electroporation, and cultured in a myoblast differentiation medium for 14 days. RNA was extracted from these cells, and fibroblasts (HDF) without gene transfer as a control, and mRNA of Myogenin gene and CKM gene was quantified by real time RT-PCR. The results are shown in FIG. 19.

The cells co-introduction with MyoD1 and L-myc genes more strongly expressed Myogenin and CKM genes as compared with the cells introduced with MyoD1 gene alone. Therefore, it was shown that transfection using plasmid vector can also induce conversion of fibroblast to myoblast by MyoD1+L-Myc gene introduction.

The invention claimed is:

1. A method for inducing a skeletal muscle cell, comprising a step of introducing MyoD family gene or an expression product thereof and Myc family gene or an expression product thereof into a somatic cell of a mammal, which is for the treatment of a disease based on a defect, deficiency or loss of function of skeletal muscle, wherein the Myc family gene is L-myc.

2. The method according to claim 1, wherein the somatic cell is a fibroblast.

3. The method according to claim 1, wherein the somatic cell is a somatic cell of human.

4. The method according to claim 1, wherein the MyoD family gene is MyoD1 gene.

5. The method according to claim 1, wherein the step of introducing MyoD family gene or an expression product thereof and Myc family gene or an expression product thereof into a somatic cell of a mammal is performed by contacting the somatic cell with a vector incorporating MyoD family gene or an expression product thereof and Myc family gene or an expression product thereof.

6. The method according to claim 1, which is used to increase the efficiency in the generation of skeletal muscle cells compared to the case wherein MyoD family gene or an expression product thereof is introduced alone.

7. The method according to claim 6, wherein the somatic cell is a fibroblast.

8. The method according to claim 6, wherein the somatic cell is a somatic cell of human.

9. The method according to claim 6, wherein the MyoD family gene is MyoD1 gene.

10. The method according to claim 6, wherein the step of introducing MyoD family gene or an expression product thereof and Myc family gene or an expression product thereof into a somatic cell of a mammal is performed by contacting the somatic cell with a vector incorporating MyoD family gene or an expression product thereof and Myc family gene or an expression product thereof.

11. The method according to claim 10, wherein the MyoD family gene is MyoD1 gene.

\* \* \* \* \*

UNITED STATES PATENT AND TRADEMARK OFFICE
CERTIFICATE OF CORRECTION

PATENT NO. : 11,242,541 B2
APPLICATION NO. : 16/474416
DATED : February 8, 2022
INVENTOR(S) : Junko Wakao et al.

Page 1 of 1

It is certified that error appears in the above-identified patent and that said Letters Patent is hereby corrected as shown below:

In the Claims

At Column 18, Lines 45-48, "which is for the treatment of a disease based on a defect, deficiency or loss of function of skeletal muscle, wherein the Myc family gene is L-myc." should be -- wherein the Myc family gene is L-myc. --.

At Column 18, Line 61, "thereof." should be -- thereof, wherein the Myc family gene is L-myc. --.

At Column 19, Line 11, "thereof." should be -- thereof, wherein the Myc family gene is L-myc. --.

Signed and Sealed this
Twenty-fifth Day of October, 2022

Katherine Kelly Vidal
*Director of the United States Patent and Trademark Office*